US011766544B2

(12) United States Patent
Kojima

(10) Patent No.: US 11,766,544 B2
(45) Date of Patent: Sep. 26, 2023

(54) VASCULAR CLOSURE DEVICE AND RELATED METHODS

(71) Applicant: Terumo Medical Corporation, Somerset, NJ (US)

(72) Inventor: Junya Kojima, Hadano (JP)

(73) Assignee: Terumo Medical Corporation, Somerset, NJ (US)

( * ) Notice: Subject to any disclaimer, the term of this patent is extended or adjusted under 35 U.S.C. 154(b) by 344 days.

(21) Appl. No.: 16/864,865

(22) Filed: May 1, 2020

(65) Prior Publication Data
US 2021/0338988 A1 Nov. 4, 2021

(51) Int. Cl.
| | |
|---|---|
| *A61M 25/10* | (2013.01) |
| *A61M 39/02* | (2006.01) |
| *A61P 7/04* | (2006.01) |

(52) U.S. Cl.
CPC ........ *A61M 25/10* (2013.01); *A61M 39/0247* (2013.01); *A61P 7/04* (2018.01); *A61M 2025/1052* (2013.01); *A61M 2039/0258* (2013.01); *A61M 2202/0425* (2013.01); *A61M 2205/15* (2013.01)

(58) Field of Classification Search
CPC ........ A61B 17/0057; A61B 2017/0061; A61B 2017/0065; A61B 2017/00659; A61M 2025/1052; A61M 2039/0258; A61M 2202/0425; A61M 2205/15; A61M 25/10; A61M 25/1002; A61M 39/0247; A61P 7/04
See application file for complete search history.

(56) References Cited

U.S. PATENT DOCUMENTS

| | | | |
|---|---|---|---|
| 5,486,195 A | * | 1/1996 | Myers ............... A61M 25/1002 606/191 |
| 5,626,601 A | | 5/1997 | Gershony et al. |
| 5,868,778 A | | 2/1999 | Gershony |
| 5,951,583 A | | 9/1999 | Jensen |
| 6,017,359 A | | 1/2000 | Gershony |
| 6,056,768 A | | 5/2000 | Cates et al. |

(Continued)

FOREIGN PATENT DOCUMENTS

| | | |
|---|---|---|
| JP | 2011508627 A | 3/2011 |
| WO | 9807372 A2 | 2/1998 |

OTHER PUBLICATIONS

Carlos F. Bechara, MD; Suman Annambhotla, MD; Peter H. Lin, MD, Access site management with vascular closure devices for percutaneous transarterial procedures, Journal of Vascular Surgery, Dec. 2010, pp. 1682-1696, vol. 52, No. 6, Houston, Texas.

(Continued)

*Primary Examiner* — Deanna K Hall
(74) *Attorney, Agent, or Firm* — Quarles & Brady LLP; James J. Aquilina

(57) ABSTRACT

The present application discloses devices and methods for performing a vascular closure procedure that comprises inserting a sheath into a tissue tract defined in a body part, temporarily sealing a vascular access site, flushing the tissue tract with a flushing fluid via the sheath, dispensing a procoagulant material into the tissue tract adjacent the vascular access site via the sheath, and then unsealing the vascular access site to cause coagulation of blood adjacent the vascular access site.

23 Claims, 25 Drawing Sheets

(56) References Cited

U.S. PATENT DOCUMENTS

| | | | | |
|---|---|---|---|---|
| 6,287,323 B1 * | 9/2001 | Hammerslag | ...... | A61B 17/0057 |
| | | | | 606/213 |
| 9,089,674 B2 | 7/2015 | Ginn et al. | | |
| 2011/0282383 A1 | 11/2011 | Vidlund et al. | | |

OTHER PUBLICATIONS

Cardinal Health, Instructions for Use—Mynx Ace Vascular Closure Device, LBL9474.A Model MX6740, Apr. 2015, pp. 1-15, Santa Clara, California.
Cardinal Health, Finish Strong; MYNXGRIP Vascular Closure Device, Cordis portfolio, Nov. 2016.
Pinnacle®, Pinnacle® Precision Access System®, Pinnacle® TIF Tip™, Sep. 2017, pp. 1-20, Terumo Medical Corporation, Elkton, Maryland.
Instructions for Use, Angio-Seal™ VIP, Vascular Closure Device, 2016, Terumo Medical Corporation, Somerset, New Jersey.
International Search Report and Written Opinion of the International Searching Authority from corresponding PCT Application No. PCT/US2021/030327, dated Aug. 17, 2021 (12 pages).
International Search Report and Written Opinion of the International Searching Authority from PCT Application No. PCT/US2021/030323, dated Aug. 19, 2021 (11 pages).

* cited by examiner

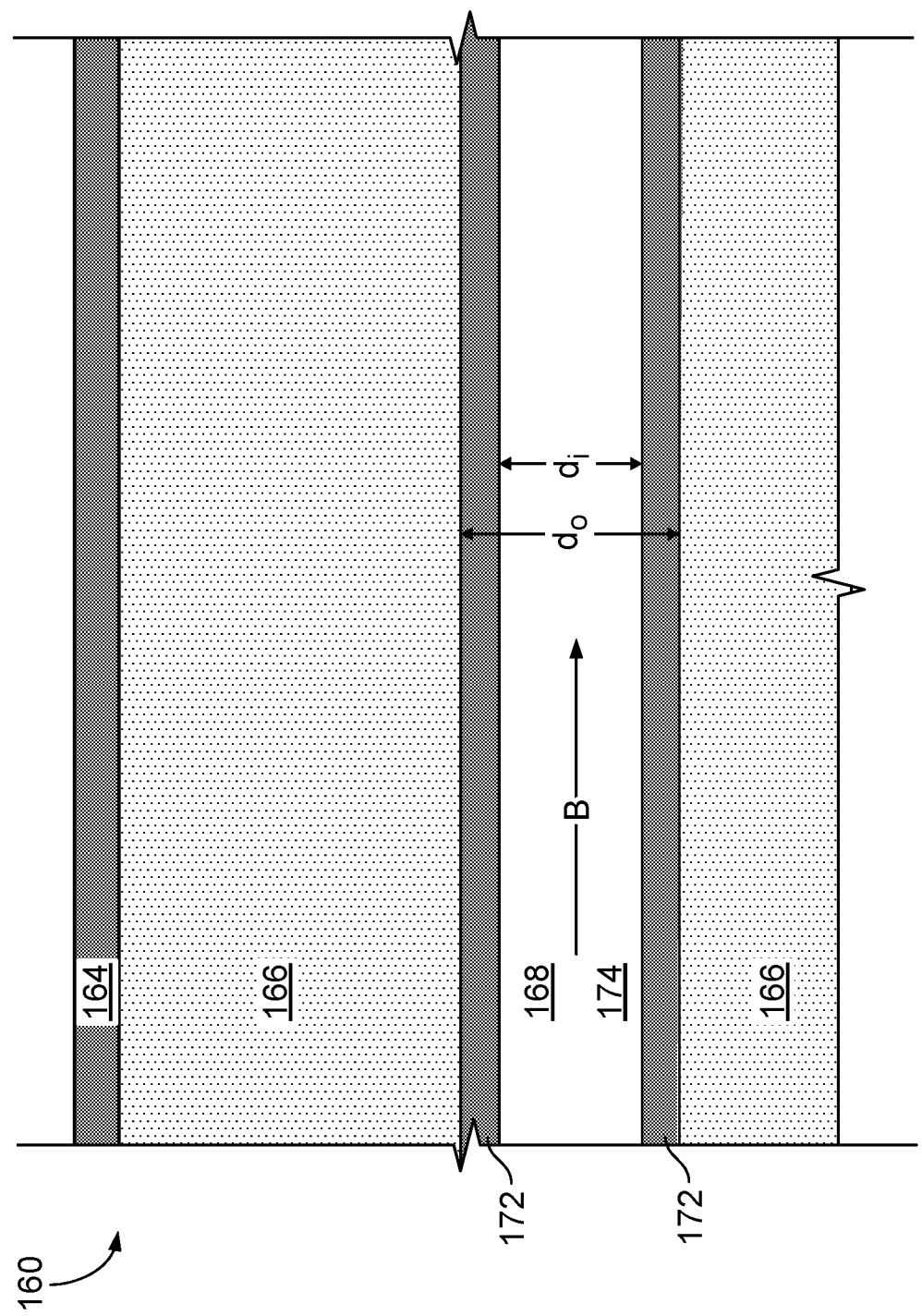

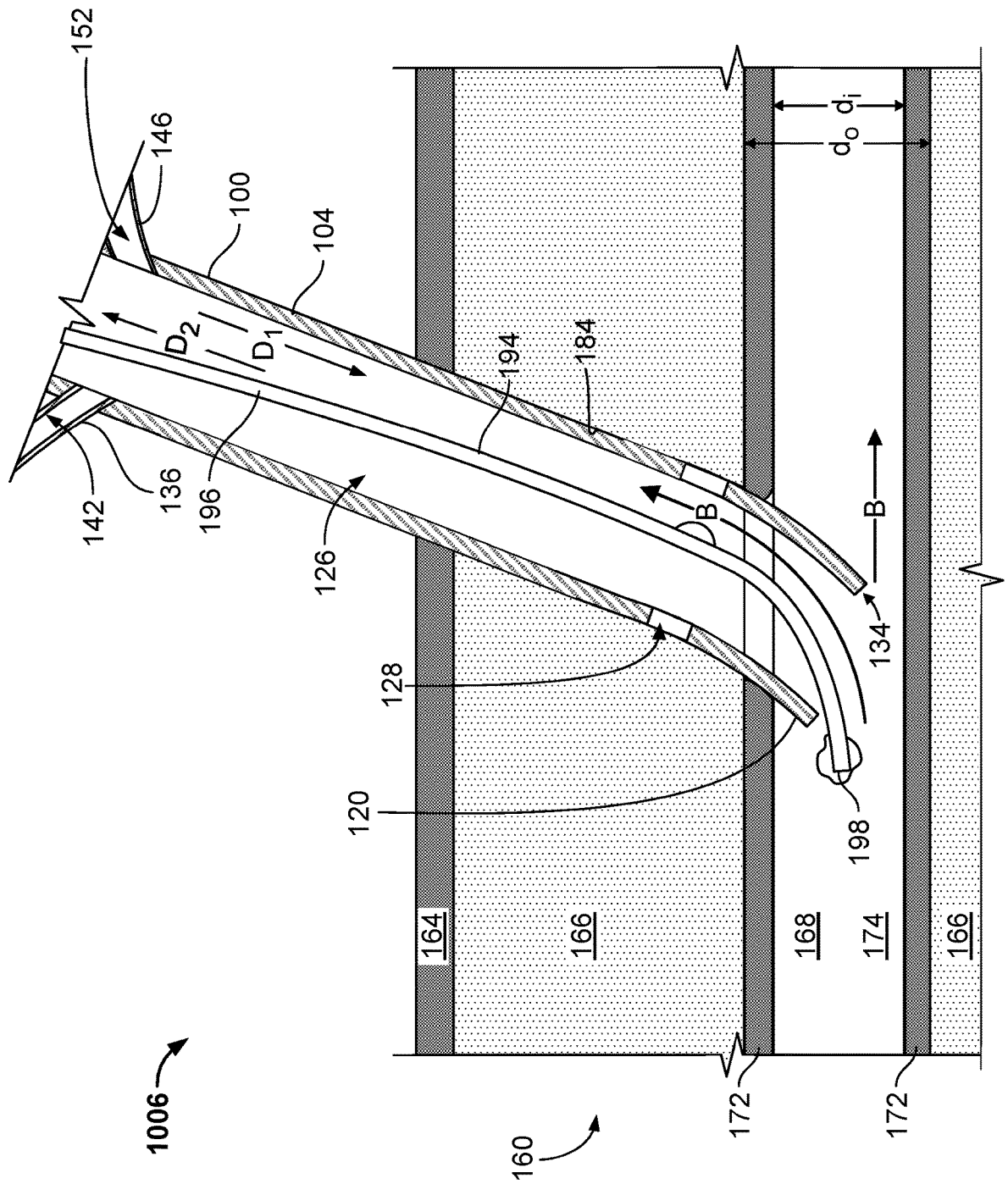

VASCULAR CLOSURE DEVICE AND RELATED METHODS

BACKGROUND

The present invention relates to a vascular closure device and related methods for achieving hemostasis at a vascular access site after a surgical procedure.

Various closure devices and methods to perform surgical procedures via blood vessel access are well known in the art. For example, in some procedures a positioning catheter may be introduced into a blood vessel via a puncture in the blood vessel, and thereafter various procedural tools (e.g., a balloon catheter) may be introduced into the blood vessel via the positioning catheter to perform a procedure at a surgical site located near or some distance away from the puncture. When the procedural tools and positioning catheter are removed, an open puncture in the blood vessel (e.g., an arteriotomy, if the blood vessel is an artery) and an open subcutaneous tissue tract will remain, and require action to prevent the patient from significant blood loss.

Various intra- and/or extra-vascular solutions for covering and sealing the arteriotomy exist. For those solutions that include an intra-vascular component, there is a risk of this component dislodging and causing an embolism. Moreover, existing solutions that include only an extra-vascular component continue to require manual compression of the access site for several minutes after removal of the devices from the tissue tract. The continued need for manual compression limits the effectiveness of these procedures and increases the time required to perform each procedure. Accordingly, there is a need for a vascular closure device and related methods that address these and other drawbacks of the prior art.

SUMMARY OF THE DISCLOSURE

In one respect, the present disclosure comprises a method of performing a vascular closure procedure at a vascular access site that has been formed through a wall of a blood vessel in a body part of a patient, the method comprising: inserting a sheath into a tissue tract defined in the body part, the tissue tract being in fluid flow communication with an interior of the blood vessel via the vascular access site such that blood from the blood vessel may enter the tissue tract; temporarily sealing the vascular access site so that blood from the blood vessel may no longer enter the tissue tract; flushing the tissue tract with a flushing fluid via the sheath such that the tissue tract is substantially cleared of blood; injecting a procoagulant material into the tissue tract via the sheath at a location adjacent the vascular access site; and unsealing the vascular access site so that blood from the blood vessel interacts with the procoagulant material at the location.

In another respect, the present disclosure comprises a vascular closure device comprising: a sheath having a wall, the wall defining a cavity, the cavity including a plurality of flush openings located in the wall adjacent a first end of the cavity and a port located at a second end of the cavity, the port and the plurality of flush openings being in fluid flow communication, the sheath being adapted to be inserted within a tissue tract defined in a body part of a patient to a position adjacent a vascular access site formed through a wall of a blood vessel in the body part, the tissue tract being in fluid flow communication with an interior of the blood vessel via the vascular access site such that blood from the blood vessel may enter the tissue tract; wherein, when the sheath is inserted within the tissue tract, a flushing fluid may be introduced into the cavity through the port such that the flushing fluid exits the cavity through the plurality of flush openings such that the sheath and the tissue tract are substantially cleared of blood.

In yet another respect, the present disclosure comprises a method of performing a vascular closure procedure at a vascular access site that has been formed through a wall of a blood vessel in a body part of a patient, the method comprising: inserting a sheath into a tissue tract defined in the body part, the tissue tract being in fluid flow communication with an interior of the blood vessel via the vascular access site such that blood from the blood vessel may enter the tissue tract; inserting a positioning catheter through the sheath into the blood vessel, the positioning catheter comprising a cavity and a nozzle slidably attached thereto such that a position of a distal end of the nozzle is adjustable with respect to a distal end of the cavity; temporarily sealing the vascular access site so that blood from the blood vessel may no longer enter the tissue tract; flushing the tissue tract with a flushing fluid via the sheath or the nozzle such that the tissue tract is substantially cleared of blood; injecting a procoagulant material into the tissue tract via the nozzle at a location adjacent the vascular access site; and unsealing the vascular access site so that blood from the blood vessel interacts with the procoagulant material at the location.

BRIEF DESCRIPTION OF THE DRAWINGS

The present disclosure will hereinafter be described in conjunction with the appended drawing figures, wherein like numerals denote like elements.

FIG. 5 is a partial cross-sectional view of the body part of FIG. 4 taken along line 5-5 of FIG. 4, showing an exemplary blood vessel on which a vascular access procedure will be performed;

FIGS. 6A and 6B are partial cross-sectional views of the exemplary vascular access device of FIGS. 1-3 and a positioning catheter in operation to close the blood vessel of FIG. 5 according to a first vascular closure method of the present disclosure;

DETAILED DESCRIPTION

Figure 1:
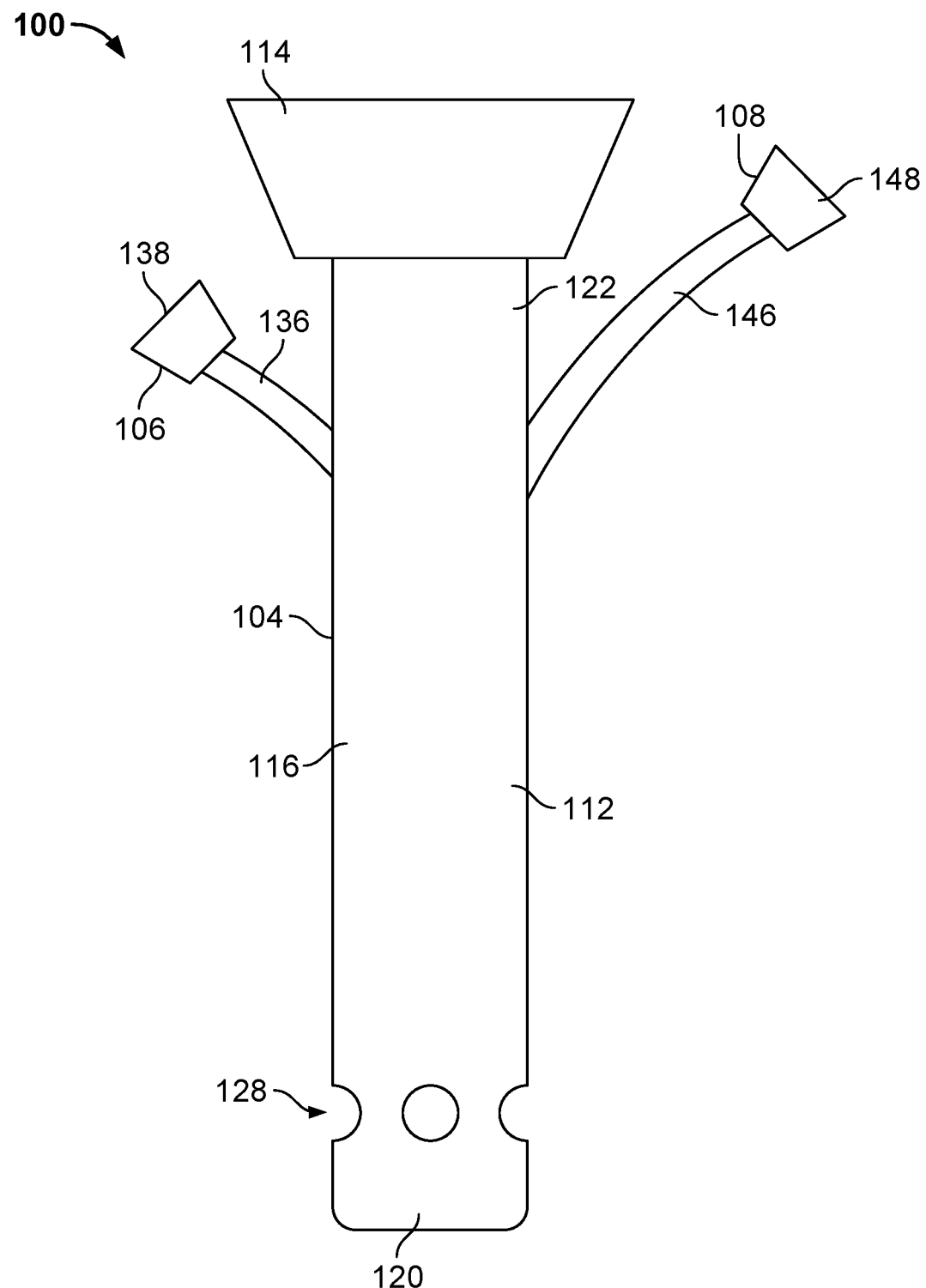
FIG. 1 is a front view of an exemplary vascular access device according to an embodiment of the present disclosure.

The ensuing detailed description provides exemplary embodiment(s) only, and is not intended to limit the scope, applicability, or configuration thereof. Rather, the ensuing detailed description of the exemplary embodiment(s) will provide those skilled in the art with an enabling description for implementing these embodiment(s). It should be understood that various changes may be made in the function and arrangement of elements of the embodiment(s) without departing from the spirit and scope of the invention, as set forth in the appended claims.

Directional terms (e.g., upper, lower, left, right, etc.) may be used herein. These directional terms are merely intended to assist in disclosing the embodiment(s) and claiming the invention and are not intended to limit the claimed invention in any way. In addition, reference numerals that are introduced in the specification in association with a drawing figure may be repeated in one or more subsequent figure(s) without additional description in the specification, in order to provide context for other features.

In the specification and accompanying claims, the terms "proximal" and "distal," unless otherwise specified, should be understood to refer to a frame of reference from the vantage of a surgeon or other clinician using the device or performing the method, with "proximal" referring to a position closer to the clinician and "distal" referring to a position closer to the vascular access site.

In the specification and accompanying claims, unless otherwise specified, the term "adjacent" should be understood to encompass both "directly in physical contact with" and also "in close proximity to." For example, with respect to the location within a tissue tract above a vascular access site where a procoagulant material comes into contact with and begins to interact with blood, unless otherwise specified, "adjacent" should be understood to mean a location both in direct physical contact with the vascular access site or otherwise in close proximity thereto.

The increased prevalence of Peripheral Arterial Disease (PAD) in patients has led to an accompanying increase in the need for peripheral interventions to attempt to clear occlusions from or surgically introduce stents into vascular pathways. Vascular access may be warranted for a number of other reasons, including surgical procedures that are to be performed some distance remote from the vascular access site. After such a procedure is complete, the vascular access site and open tissue tract through which access to the blood vessel was gained must be closed to prevent significant blood loss from the patient.

Various intra- and/or extra-vascular solutions for covering and sealing an arteriotomy and other vascular access sites (e.g., venous access sites) exist. For those solutions that include an intra-vascular component, there is a risk of this component dislodging and causing an embolism or other complications. Moreover, existing solutions that include only an extra-vascular component continue to require compression of the access site for several minutes after removal of the devices from the tissue tract—whether manually or via a pressure-supplying device (e.g., a band with an inflatable balloon assembly)—because the sealing of the arteriotomy provided by these extra-vascular devices is imperfect such that blood will continue to leak from the arteriotomy. The continued need for the use of compression after the implantation of such extra-vascular closure devices limits the effectiveness of these procedures and increases the amount of time necessary to perform each procedure. Moreover, the imperfect extra-vascular adhesion and sealing caused by existing devices and methods may lead to vascular complications, for example hematomas and pseudoaneurysms.

Currently, a vascular closure device and related methods that reduce and/or eliminate the need to apply pressure to a vascular access site without the need to leave any sealing component in an intravascular position after a vascular access procedure is not believed to exist. The present disclosure describes a new vascular access device and related methods that are specifically configured to close a vascular access site with little to no application of pressure and without the need to leave an intravascular sealing component.

The device and methods according to the present disclosure provide improvements through the delivery of procoagulant material (e.g., a fluid or gel) as close as possible to the arteriotomy, which leads to improved adhesion of the partially-coagulated plug of mixed blood and procoagulant to the extravascular portion of the blood vessel atop the arteriotomy, as well as more complete filling of the subcutaneous tissue tract. In both respects, the device and methods according to the present disclosure provide improvements over the known prior art, in which procoagulant is delivered into the tissue tract from a position remote from the arteriotomy (e.g., via a sidearm of a positioning catheter that is located well above the skin surface), which leads to coagulation well up in the cavity of the sheath or tissue tract (i.e., far from the arteriotomy), which is believed to reduce the quality and adhesive effectiveness of the plug formed by the mixed blood and procoagulant material. The inventor has conceived of multiple methods of delivering a procoagulant material at or adjacent to the arteriotomy through various filling and injection methods, which causes the procoagulant material to mix with fresh blood exiting the arteriotomy and results in improved coagulation and reduced or eliminated need for the later application of pressure to the vascular access site to achieve hemostasis.

The present application discloses various methods of filling the tissue tract with a procoagulant material. A counterpart application having the same named inventor, applicant, and title—and which is being filed on the same date as the present application—discloses various methods of injecting the tissue tract with a procoagulant material. It should be understood that said counterpart application is incorporated herein by reference as if set forth in its entirety.

The procoagulant material used according to any of the embodiments herein may be in the form of a liquid, viscous liquid, suspension, gel, foam, or a mixture of any thereof. Suitable compounds for the procoagulant material include, but are not limited to, cyanoacrylate (CA), polyurethane, thrombin, a mixture of thrombin and collagen, a mixture of thrombin and gelatin, a mixture of thrombin and fibrinogen, and mixtures of any thereof. The procoagulant material(s) may also be mixed with a solvent, for example but not limited to dimethyl sulfoxide (DMSO), to form a procoagulant mixture that is in a viscous liquid, suspension, gel, or foam form, or a mixture of two or more of these forms. Further, in various methods according to the present disclosure, the solvent and procoagulant may be introduced together into the tissue tract and/or adjacent to the arteriotomy in a variety of orders, for example: the solvent is introduced immediately after the procoagulant material; the procoagulant material is introduced immediately after the solvent; the solvent and procoagulant material are introduced at alternating times in three or more steps (e.g., procoagulant-solvent-procoagulant-etc. or solvent-procoagulant-solvent-etc.; or the procoagulant material and the solvent are introduced simultaneously.

Figure 2:
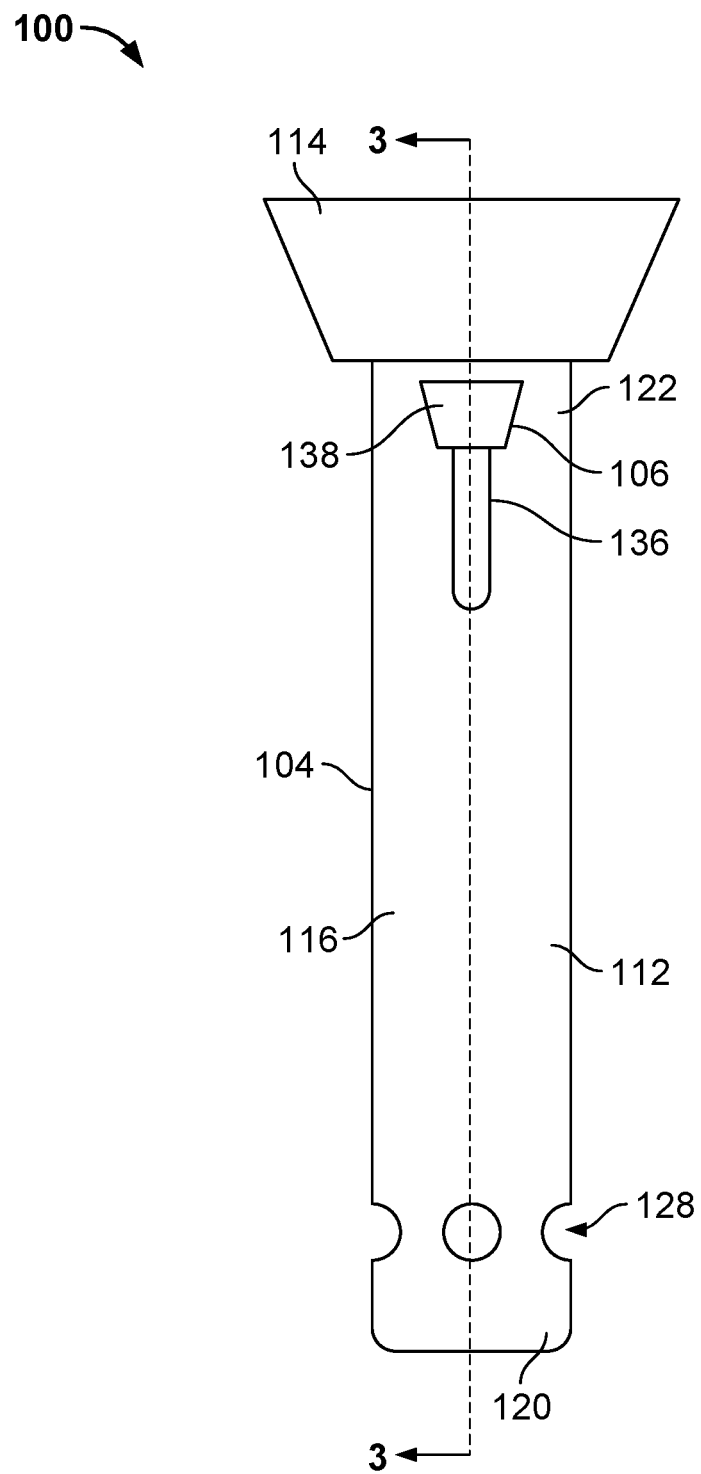
FIG. 2 is a side view thereof.
Figure 3:
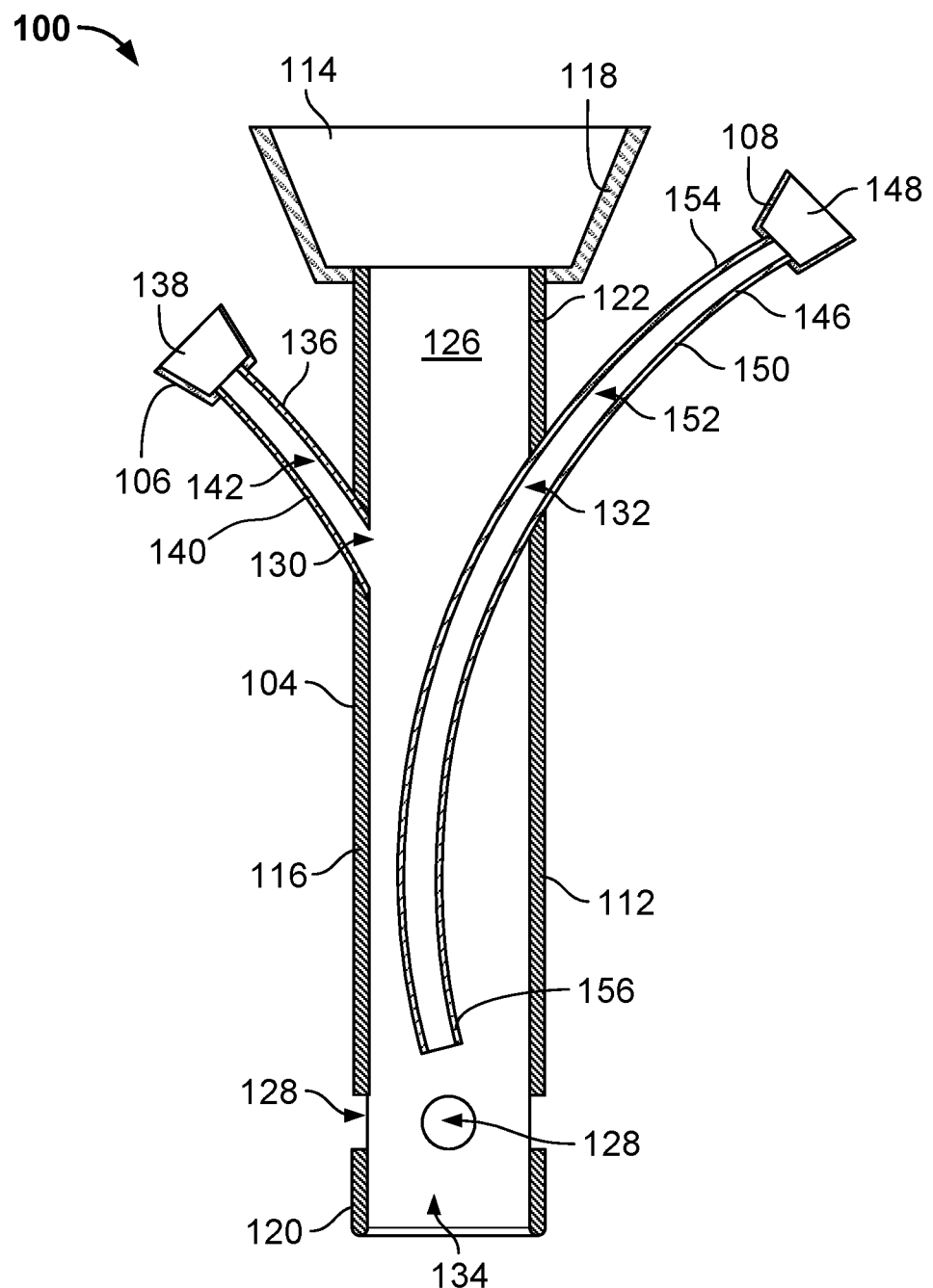
FIG. 3 is a cross-sectional view thereof, taken along line 3-3 of FIG. 2.

Referring generally to FIGS. 1-3 and 6A-10, a first embodiment of a vascular access device 100 according to the above-noted inventive concept will be described in detail below. In addition, FIGS. 12-17 show a second embodiment of a vascular access device 100' according to the above-noted inventive concept. It should be understood that all parts in the vascular access device 100' bearing the same reference numerals as the respective parts in the vascular access device 100 are functionally identical thereto, unless otherwise discussed herein. Accordingly, the vascular access device 100' will not be described in detail below, and the discussion below of the vascular access device 100 should be understood to also apply to the vascular access device 100, mutatis mutandis. As shown in FIGS. 1-3, in this embodiment the vascular access device 100 is designed to deliver blood procoagulant (e.g., via a filling step or injecting step) to a location at or very near a vascular access site, as shown in FIGS. 6A-18 and as would be understood by a person having ordinary skill in the art. With reference to FIGS. 1 and 3, the vascular access device 100 includes a sheath 104, an indicator 106 (e.g., a blood flow indicator), and a nozzle 108.

With reference to FIGS. 1 and 3, the sheath 104 includes a first tube 112 and a first port 114. In this embodiment, the first port 114 is partially conical in shape and includes a top opening 118 through which diagnostic or procedural tools (e.g., a positioning catheter) may be introduced into the blood vessel 168. Alternative shapes for the first port 114 and top opening 118 are possible without departing from the scope or spirit of the present disclosure. In the present embodiment, the first tube 112 is defined by a wall 116 (which in this embodiment is annular in shape, but is capable of alternative shapes), a first end 120 located distal (i.e., with respect to the vantage point of the clinician), and a second end 122 located proximal. The first port 114 is connected to the first tube 112 at the second end 122. With reference to FIG. 3, the wall 116 of the sheath 104 defines a first cavity 126 interior thereto. The wall 116 further defines a plurality of flush openings 128 located near the first end 120 thereof (present in the dedicated sheath form of the vascular access device 100 only, but not present in the procedure sheath form of the vascular access device 100'), an indicator opening 130, and a nozzle opening 132, each of which extend through the wall 116. The first tube 112 includes a bottom opening 134 located at the first end 120, the bottom opening 134 adapted to be placed adjacent the arteriotomy. Each of the top opening 118, the flush openings 128, the indicator opening 130, the nozzle opening 132, and the bottom opening 134 are in fluid flow communication with the first cavity 126 of the sheath 104. In the present embodiment, the wall 116 is eased (e.g., radiused, rounded, chamfered, etc.) at the first end 120 to remove sharp edges, since the first end 120 is designed to be inserted into a tissue tract and into the blood vessel 168, as well as being placed adjacent an arteriotomy, including in direct physical contact therewith.

Referring again to FIG. 3, in this embodiment the flush openings 128 are evenly circumferentially arranged about the wall 116 near the first end 120 thereof. In the present embodiment, four flush openings 128 are envisioned, although any number of flush openings could be provided in alternative embodiments, and the flush openings 128 need not be evenly circumferentially arranged about the wall 116. In the present embodiment, the nozzle opening 132 is located opposite the indicator opening 130 in the wall 116 and at approximately the same position along the length of the first tube 112, significantly closer to the second end 122 than the first end 120. Multiple alternative positions for the indicator opening 130 and/or the nozzle opening 132 are possible, as would be understood by a person having ordinary skill in the art. As noted above, no flush openings are present in the procedure sheath form of the vascular access device 100' shown in FIGS. 12-17.

With further reference to FIG. 3, the indicator 106 includes a second tube 136 and a second port 138 connected to the second tube 136 at a proximal end thereof. In this embodiment, the second port 138 is partially conical in shape, although alternative shapes are possible. The second tube 136 includes a wall 140 (which in this embodiment is annular in shape, but is capable of alternative shapes) that, along with the second port 138, defines a second cavity 142 that is in fluid flow communication with the first cavity 126 of the sheath 104. The indicator 106 is mounted to the sheath 104 via the connection of the second tube 136 to the sheath 104 at the indicator opening 130. In some embodiments, the indicator 106 is formed of a transparent or translucent material (e.g., polymer plastic and/or glass). Thus, a clinician may view whether blood has traveled up the sheath 104 and is present in the indicator 106. The indicator 106 allows for the clinician to check for blood back flow into the sheath 104 when the sheath 104 is inserted into the blood vessel 168. In alternative embodiments, the indicator 106 may be omitted entirely or provided as a completely separate device.

With further reference to FIG. 3, the nozzle 108 includes a third tube 146 and a third port 148 attached at a top end 154 (i.e., proximal end) thereof. In this embodiment, the third port 148 is partially conical in shape, although alternative shapes are possible. The third tube 146 includes a wall 150 (which in this embodiment is annular in shape, but is capable of alternative shapes) which, along with the third port 148, defines a third cavity 152 interior thereto. In this embodiment, the third tube 146 is flexible and slidably engaged with the sheath 104 such that a bottom end 156 (i.e., distal end) of the third tube 146 may be adjustably relocated either close to or remote from the bottom opening 134 of the sheath 104. The third cavity 152 is in fluid flow communication with the first cavity 126, so that procoagulant and other components (e.g., flushing liquids) may be introduced into the first cavity 126 via the third cavity 152, as will be further described below.

Referring still to FIG. 3, and as mentioned above, the nozzle 108 is slidably engaged with the sheath 104. More specifically, in operation the length of the third tube 146 may be slid through the wall 116 via the nozzle opening 132 to selectively approach and retract the bottom end 156 of the third tube 146 relative to the first end 120 of the sheath 104 within the first cavity 126. In addition, in the present embodiment, the third tube 146 may be slidably positioned in the sheath 104 such that the bottom end 156 of the third tube 146 extends beyond the first end 120 of the sheath 104, through the bottom opening 134.

Figure 4:
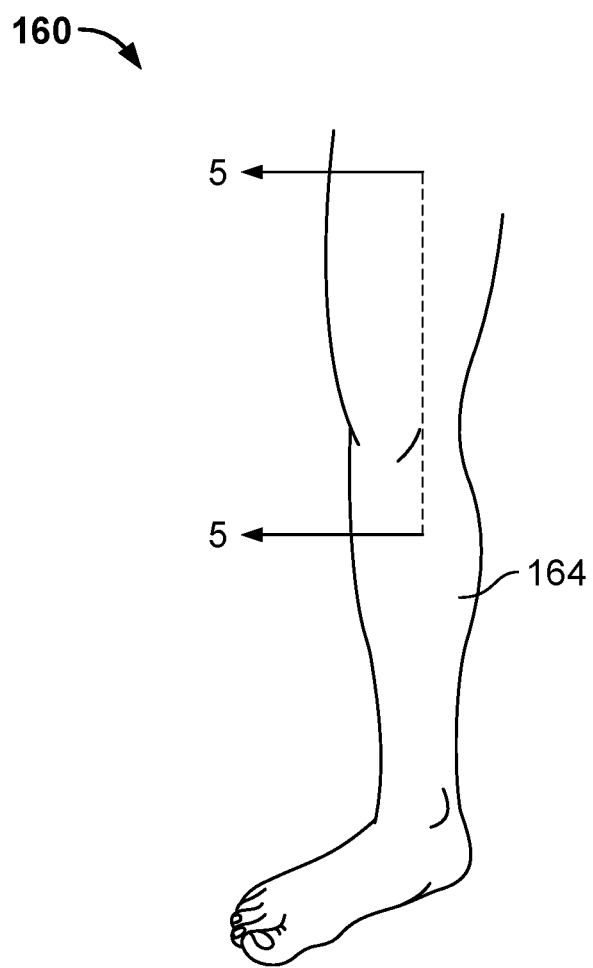
FIG. 4 is a perspective view of an exemplary body part of a patient where a vascular access procedure may occur.

With reference to FIG. 4, an exemplary body part 160 where a vascular access procedure is to be performed, e.g., a leg, is illustrated. The body part 160 includes skin 164. With reference to FIG. 5, the body part 160 also includes a blood vessel 168 (e.g., an artery) where the vascular access procedure is to be performed and tissue 166 (e.g., one or more of muscle, fat, connective tissue, fascia, membranous layers, etc.) that surrounds the blood vessel 168 both above (i.e., towards the surface of the skin 164) and below. In some cases, it should be understood, bone might instead be located immediately below the targeted blood vessel instead of tissue 166. In either scenario, a properly-executed vascular access procedure involves accessing the interior of the blood vessel 168 (e.g., a fourth cavity 174) through a wall 172 thereof, without puncturing through the other side thereof (i.e., puncturing through the blood vessel wall 172 located closer to the skin 164 in FIG. 5, without puncturing the opposite side of the blood vessel wall 172 located further away from the skin 164). The blood vessel wall 172 is generally cylindrical and thus has an inner diameter $d_i$ and an outer diameter $d_o$. A flow of blood B courses through the blood vessel 168, and exerts outward pressure on the inner diameter $d_i$ of the blood vessel wall 172.

Various vascular access procedures are well-known in the art. A commonly-used procedure is known as the Seldinger Technique ("ST"). In the first step of the ST, a hollow needle (cannula) is inserted in a first direction $D_1$ (see the arrow indicating the first direction $D_1$ in FIG. 6A) through the skin 164, tissue 166, and blood vessel wall 172, thus opening a tissue tract 184 in the skin 164 and the tissue 166 and an arteriotomy 186 that is defined in the blood vessel wall 172. In the next step of the ST, a guidewire or leader is introduced in the first direction $D_1$ through the interior of the hollow needle and placed interior to the blood vessel 168. The hollow needle is then removed from the tissue tract 184, leaving the guidewire in place to maintain vascular access.

During known treatment methods, a procedure sheath is then introduced over the guidewire and into the interior of the blood vessel 168. The procedure sheath is then used to permit the introduction of diagnostic and/or interventional tools into the interior of the blood vessel 168, which are then removed from the procedure sheath upon completion of the intended procedure(s).

In the methods according to the present disclosure, either the procedure sheath may be used continuously throughout performance of the vascular closure methods discussed herein, or in the alternative the procedure sheath is removed from the tissue tract after the diagnostic and/or interventional procedures have been performed and is replaced with a dedicated sheath prior to the vascular closure steps discussed herein. If a dedicated sheath is to be used for the vascular closure methods, it is first introduced over a guidewire (which will need to be reintroduced, if previously removed) using a dilator to access the interior of the blood vessel 168, prior to performance of the vascular closure methods discussed herein.

FIGS. 6A-11 illustrate various steps of a vascular closure method 1006 which comprises the step of filling the sheath 104 with procoagulant close to the arteriotomy 186, while the sheath 104 is located in a distal position adjacent to (e.g., in direct physical contact with or in close proximity to) the blood vessel 168. With reference to FIG. 6A, as part of method 1006, while the vascular access device 100 is located partially interior to the blood vessel 168, a positioning catheter 194 (e.g., a balloon catheter) is introduced into the blood vessel 168 via the vascular access device 100. More specifically, positioning catheter 194 is slid through the sheath 104 in the first direction $D_1$ to enter the blood vessel 168 via the tissue tract 184 and the arteriotomy 186. The sheath 104 guides and directs the positioning catheter 194 into the blood vessel 168, while in its uninflated/unexpanded state. In this embodiment, the positioning catheter 194 includes a fourth tube 196 connected to a balloon 198. As further described below, the balloon 198 is selectively inflatable via the fourth tube 196. During this step, a portion of the flow of blood B from the blood vessel 168 is able to freely flow through the arteriotomy 186 and into the sheath 104.

Figure 6B:
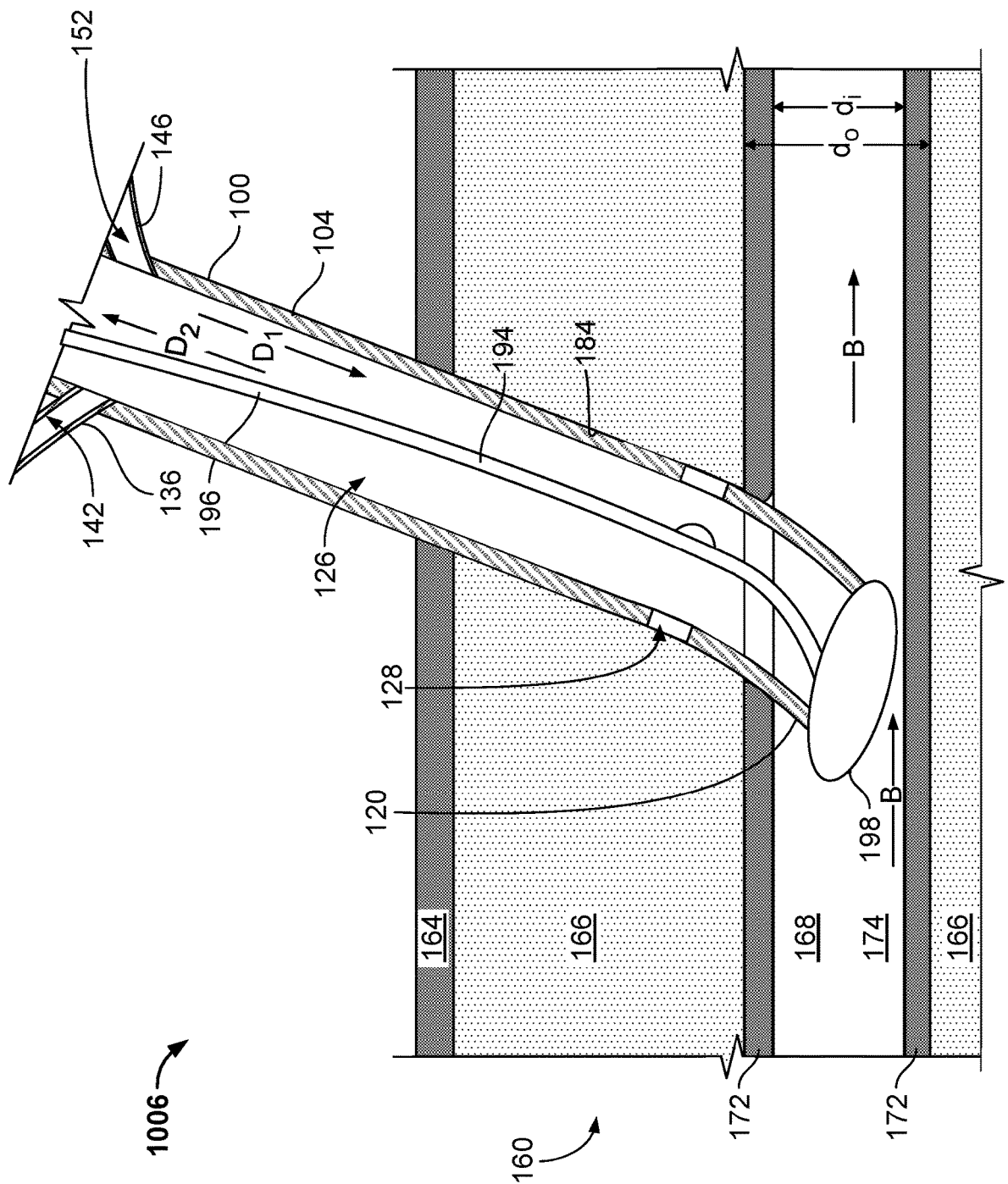
Figure 7:
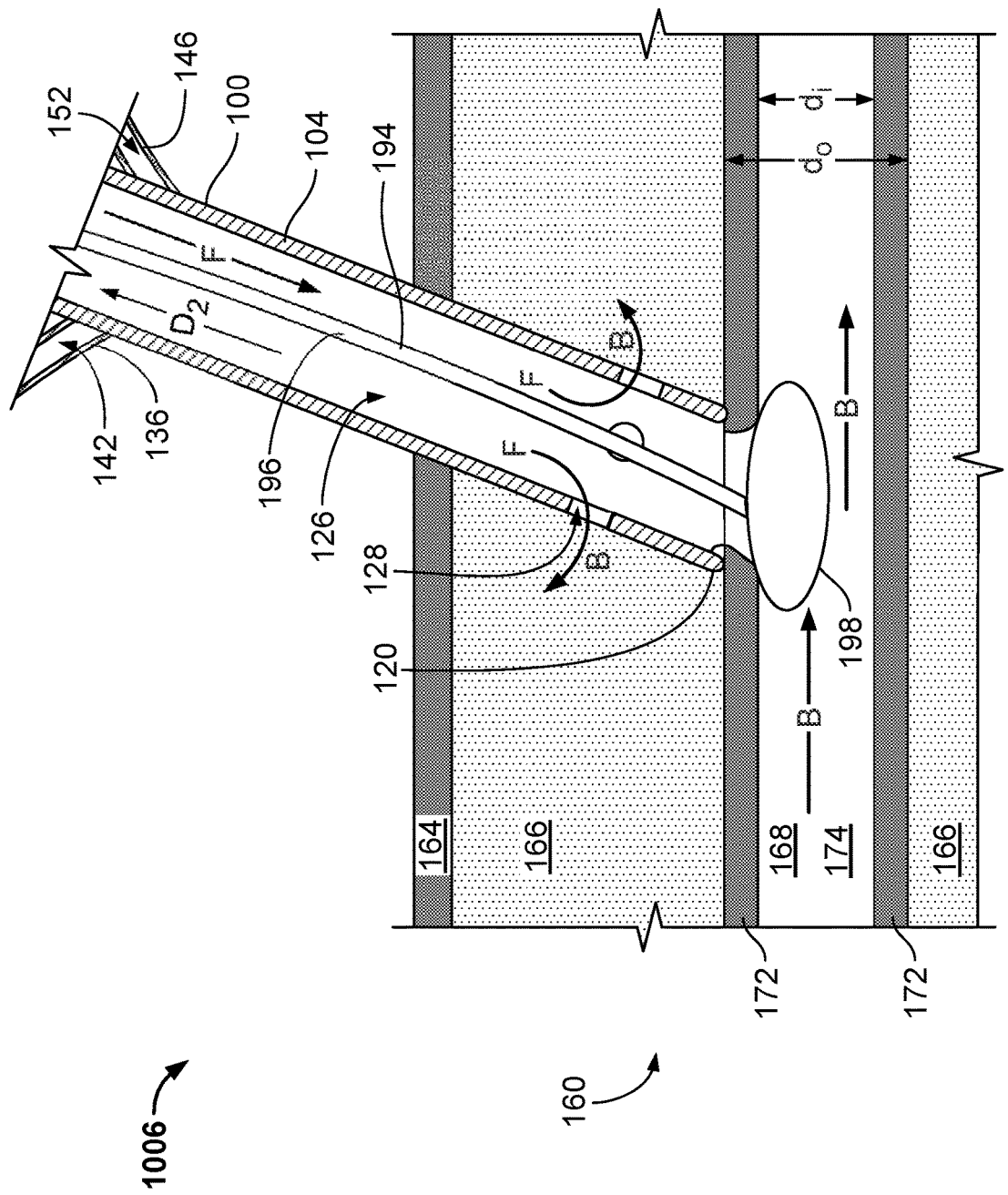
FIG. 7 is a partial cross-sectional view of the exemplary vascular access device of FIGS. 1-3 and the positioning catheter of FIGS. 6A and 6B further in operation to close the blood vessel of FIGS. 5-6B according to the first vascular closure method.

With reference to FIG. 6B, in further operation of method 1006, the balloon 198 is inflated (e.g., with saline and/or air) via the fourth tube 196 and then pulled in the second direction $D_2$ so that the balloon 198 in its inflated state abuts and seals off the first end 120 of the vascular access device 100 so that no additional blood B can flow into the sheath 104. The sheath 104 and positioning catheter 194 are then simultaneously pulled in the second direction $D_2$ until the inflated balloon 198 abuts the inner diameter $d_i$ of the blood vessel wall 172 and the sheath 104 is located in an extravascular position adjacent the arteriotomy 186, as shown in FIG. 7. As the inflated balloon 198 contacts the inner diameter $d_i$, it impedes the flow of blood B from flowing out of blood vessel 168 via the arteriotomy 186. In other words, the balloon 198 lodges against and covers the inner diameter $d_i$ at the arteriotomy 186, and is held in place in this position for additional steps of the method. It should be further understood that, in alternative embodiments according to the present disclosure, other types of devices (e.g., anchor-type devices) capable of temporarily sealing the arteriotomy 186 (i.e., for performing a temporary sealing step and an unsealing step) could be employed instead of an inflatable-balloon type device.

As noted above, the present application discloses novel methods 1006,1106 of performing a vascular closure procedure that involve filling a sheath or the tissue tract with a procoagulant component close to the arteriotomy while the arteriotomy is temporary closed, and then reopening the arteriotomy so that blood exiting a blood vessel through the arteriotomy immediately reacts with the procoagulant located in the sheath or tissue tract. While the vascular closure device 100 according to the present disclosure may be used to practice these methods, it is not essential that this exact device be employed to perform the methods described herein. As would be understood by a person having ordinary skill in the art from a review of the present application, any suitable device having a sheath with suitably-located flushing opening(s) close to the distal end thereof and a means for delivery of procoagulant close to an arteriotomy could be employed instead, within the spirit and scope of the present disclosure. For example, a separate micro-catheter, nozzle, or the fourth tube 196 of the positioning catheter 194 could alternatively be employed to deliver the flushing liquid and/or the procoagulant material to the arteriotomy 186. In an alternative example, a positioning catheter could be provided with a nozzle slidably attached to the fourth tube 196 (i.e., primary cavity) thereof that is used to deliver the procoagulant to the arteriotomy, wherein the nozzle has a distal end that is adjustable with respect to the distal end of the primary cavity of the positioning catheter such that the distal end of the nozzle can be adjusted to positions located near, at, and/or beyond the distal end of the primary cavity of the positioning catheter. Further, both existing dedicated sheaths and procedure sheaths having one or more distally-located hole(s) located therein could be used to perform the methods 1006,1106 according to the present disclosure. For the methods 1006,1106 taught in the present application, the flushing fluid or solution F and/or procoagulant material C can be introduced in close proximity to the arteriotomy 186 through a micro catheter or other small nozzle that has been passed through the valve port of a procedure sheath. Further, in some embodiments according to the present methods 1006,1106, it may be desirable to ensure that the procoagulant material C is introduced (i.e., in the first direction $D_1$) to the arteriotomy 186 at a pressure less than the combined pressure of the blood pressure in the flow of blood B and the pressure with which the balloon is being pulled against the inner diameter $d_i$ of the blood vessel 168 at the arteriotomy 186 (i.e., the combined pressure acting in the second direction $D_2$), to minimize the risk of the procoagulant material C entering the blood vessel 168 and possibly causing an embolic event.

Figure 8:
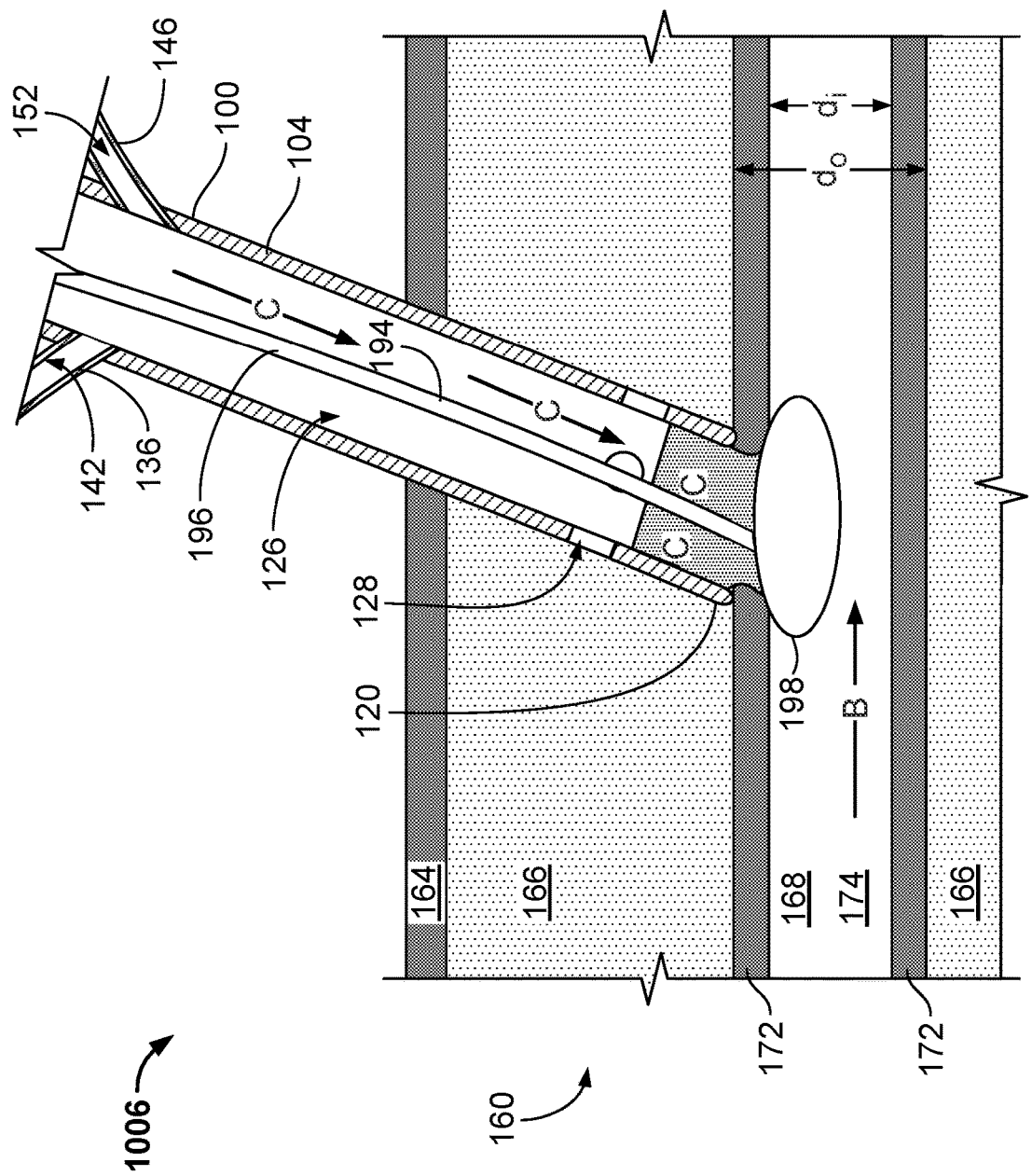
FIG. 8 is a partial cross-sectional view of the exemplary vascular access device of FIGS. 1-3 6A, and 6B and the positioning catheter of FIGS. 6A-7 in yet further operation to close the blood vessel of FIGS. 5-7 according to the first vascular closure method.

Referring back to FIG. 7, in further operation of method 1006, while the balloon 198 remains inflated against the interior side of the arteriotomy 186, the tissue tract 184 and the arteriotomy 186 are flushed using a flushing fluid F, which may be for example saline, an organic solvent, or a procoagulant solution. More specifically, flushing fluid F is injected into the sheath 104 (either via the first port 114 or the third port 148), and this flushing fluid F—along with any blood B that has collected within the sheath 104—flows out of the flush openings 128 and/or the bottom opening 134 into the tissue tract 184, but preferably does not enter the interior of the blood vessel 168 (and likely will not due to the placement of the inflated balloon 198 and the internal pressure of the flow of blood B through the blood vessel 168, so long as the flushing fluid F is added at a pressure less than the combined pressure of the balloon 198 as it is being pulled and the blood pressure in the flow of blood B, as noted above). As a result of this step, little to no blood will remain in the sheath 104 or tissue tract 184 because the arteriotomy 186 is temporarily sealed. With reference to FIG. 8, in further operation of method 1006, procoagulant fluid C is then introduced into the sheath 104 so that it fills the space atop and within the arteriotomy 186 and sits atop the inflated balloon 198.

In various alternative embodiments according to the present disclosure, the procoagulant fluid C could be introduced according to any of the following concepts: at multiple points between the distal and proximal ends of the sheath 104 at the same time; at multiple points between the distal and proximal ends of the sheath 104 at different times; while moving the first end 120 of the sheath 104 from the distal side to the proximal side of the tissue tract 184; and/or while moving the first end 120 of the sheath 104 from the proximal side to the distal side of the tissue tract 184.

Figure 9:
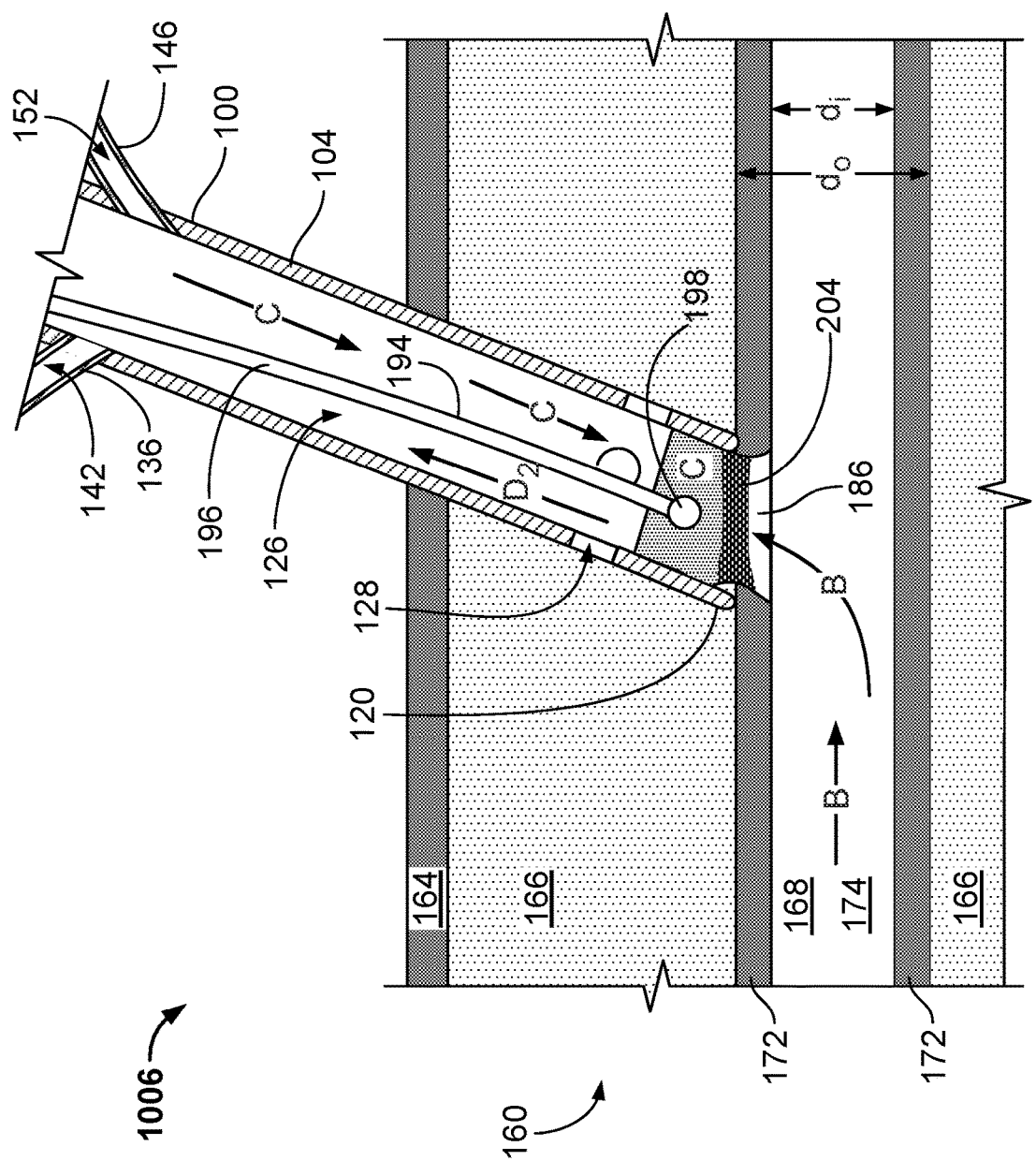
FIG. 9 is a partial cross-sectional view of the exemplary vascular access device of FIGS. 1-3 and 6A-8 and the positioning catheter of FIGS. 6A-8 in even further operation to close the blood vessel of FIGS. 5-8 according to the first vascular closure method.

With reference to FIG. 9, in further operation of method 1006, the positioning catheter 194 is now removed from the body part 160. More specifically, the balloon 198 is deflated and pulled in the second direction $D_2$, through the pooled procoagulant fluid and out of the vascular access device 100, thus unsealing the vascular access site. When the balloon 198 is deflated, a portion of the flow of blood B immediately flows into the arteriotomy 186, where it makes contact with the procoagulant fluid C, thus starting the coagulation process and forming a partially-coagulated plug 204. The remainder of the procoagulant fluid C located in the sheath 104 will also quickly coagulate, starting at the arteriotomy 186 and continuing proximally towards the skin 164.

Figure 10:
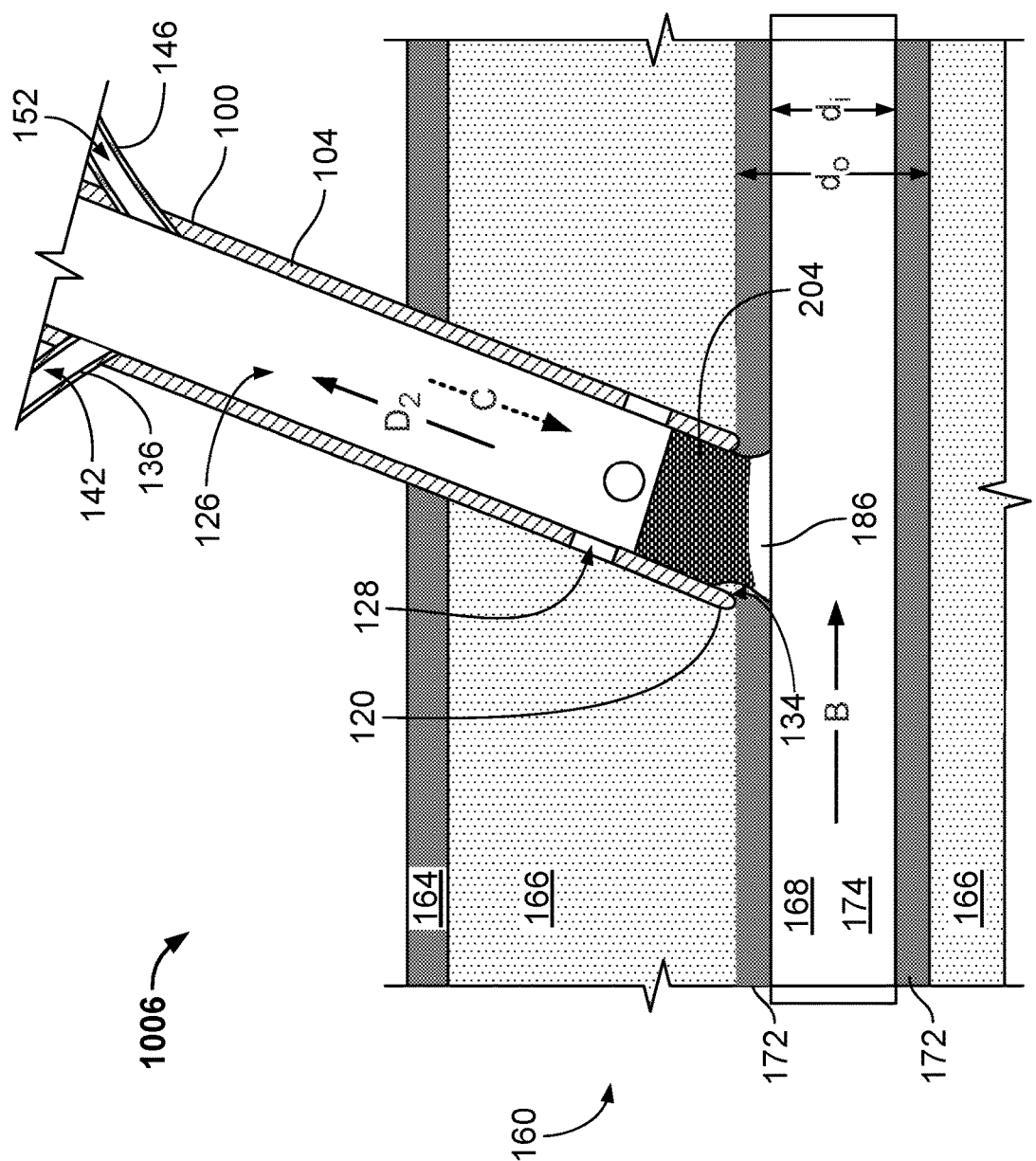
FIG. 10 is a partial cross-sectional view of the exemplary vascular access device of FIGS. 1-3 and 6A-9 in further operation to close the blood vessel of FIGS. 5-9 according to the first vascular closure method.

With reference to FIG. 10, in further operation of method 1006, the vascular access device 100 is now removed from the body part 160. More specifically, the vascular access device 100 is pulled in the second direction $D_2$ and completely removed from the tissue tract 184. If necessary, additional procoagulant material C may optionally be filled within the tissue tract 184 to a level closer to the skin 164 than what is shown in FIGS. 8-11, including filling the entire tissue tract 184 up to the surface of the skin 164. If additional procoagulant material is introduced, it may be desirable to ensure that the procoagulant material C is introduced (i.e., in the first direction $D_1$) at a pressure less than the blood pressure in the flow of blood B (i.e., the pressure acting in the second direction $D_2$), to minimize the risk of the procoagulant material C entering the blood vessel 168 and possibly causing an embolic event.

Figure 11:
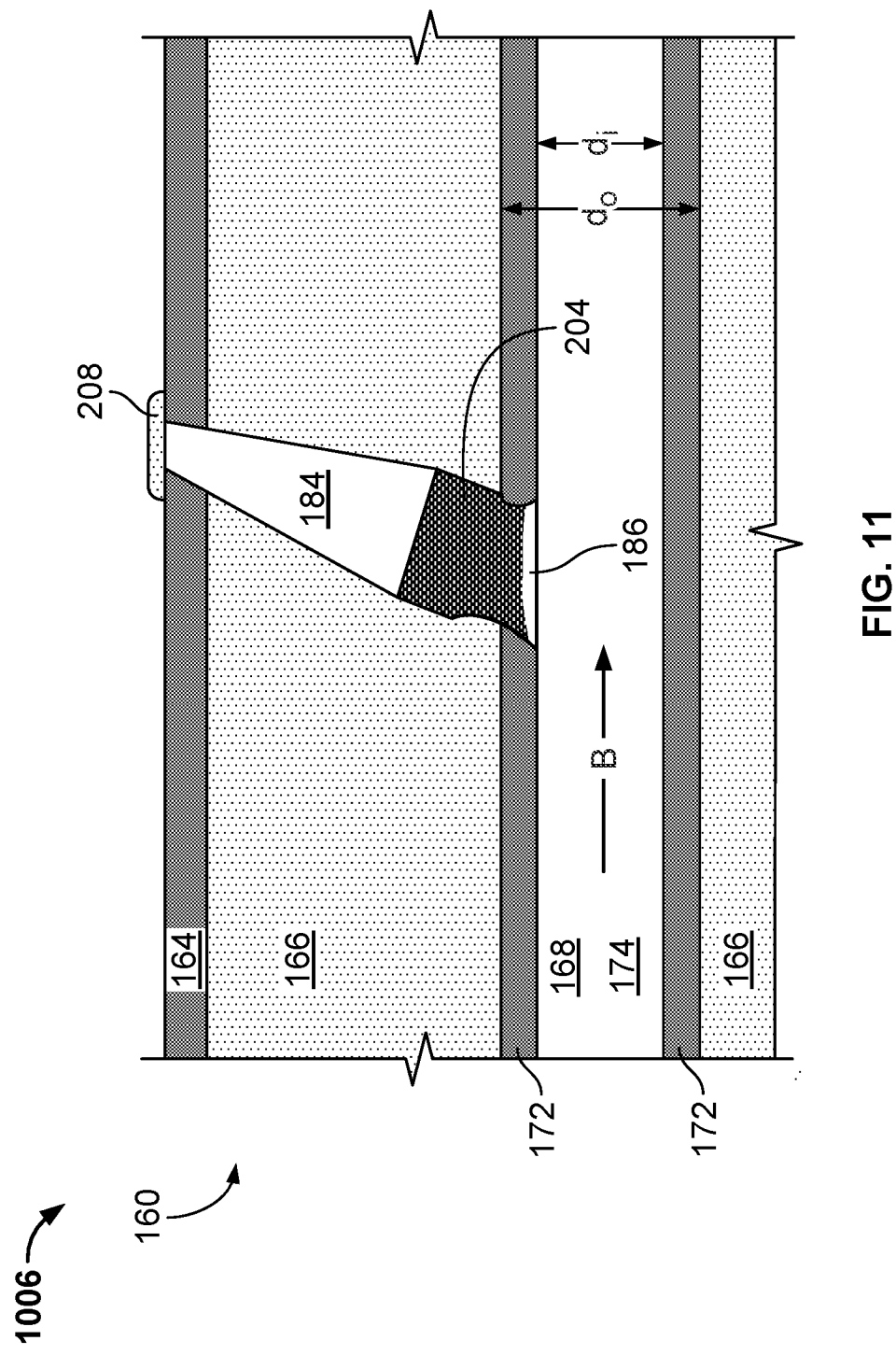
FIG. 11 is a partial cross-sectional view of a bandage in operation to close the body part of FIGS. 4-10 according to the first vascular closure method.

With reference to FIG. 11, a bandage 208 may finally be applied to the skin 164 to cover and close the tissue tract 184 at the skin 164 end thereof. Thus, the plug 204 closes the arteriotomy 186 and the bandage 208 closes the tissue tract 184.

Figure 12:
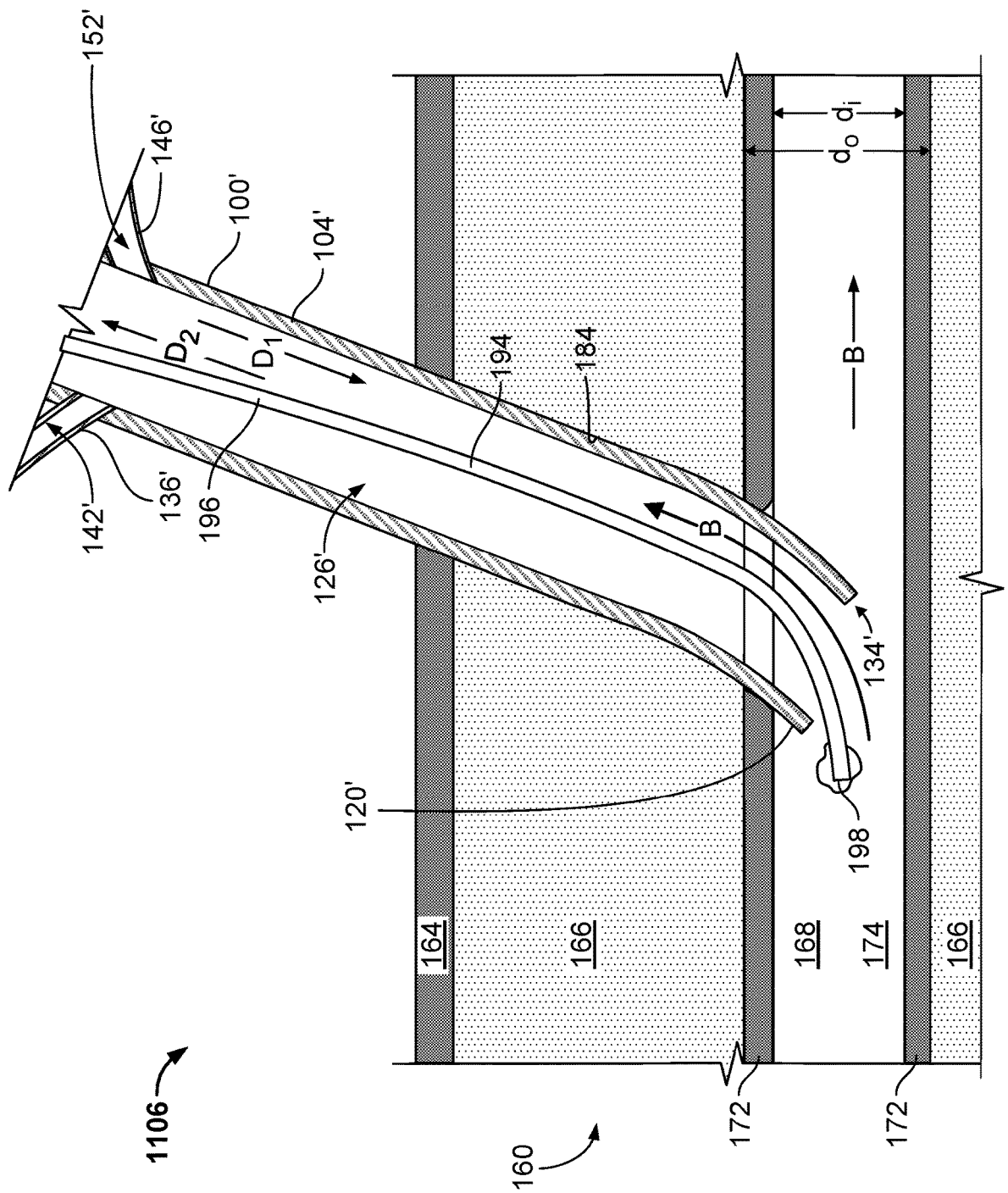
FIG. 12 is a partial cross-sectional view of an alternative vascular access device according to the vascular access device of FIGS. 1-3 and 6A-10 and the positioning catheter of FIGS. 6A-9 in operation to close the blood vessel of FIG. 5 according to a second vascular closure method of the present disclosure.
Figure 13:
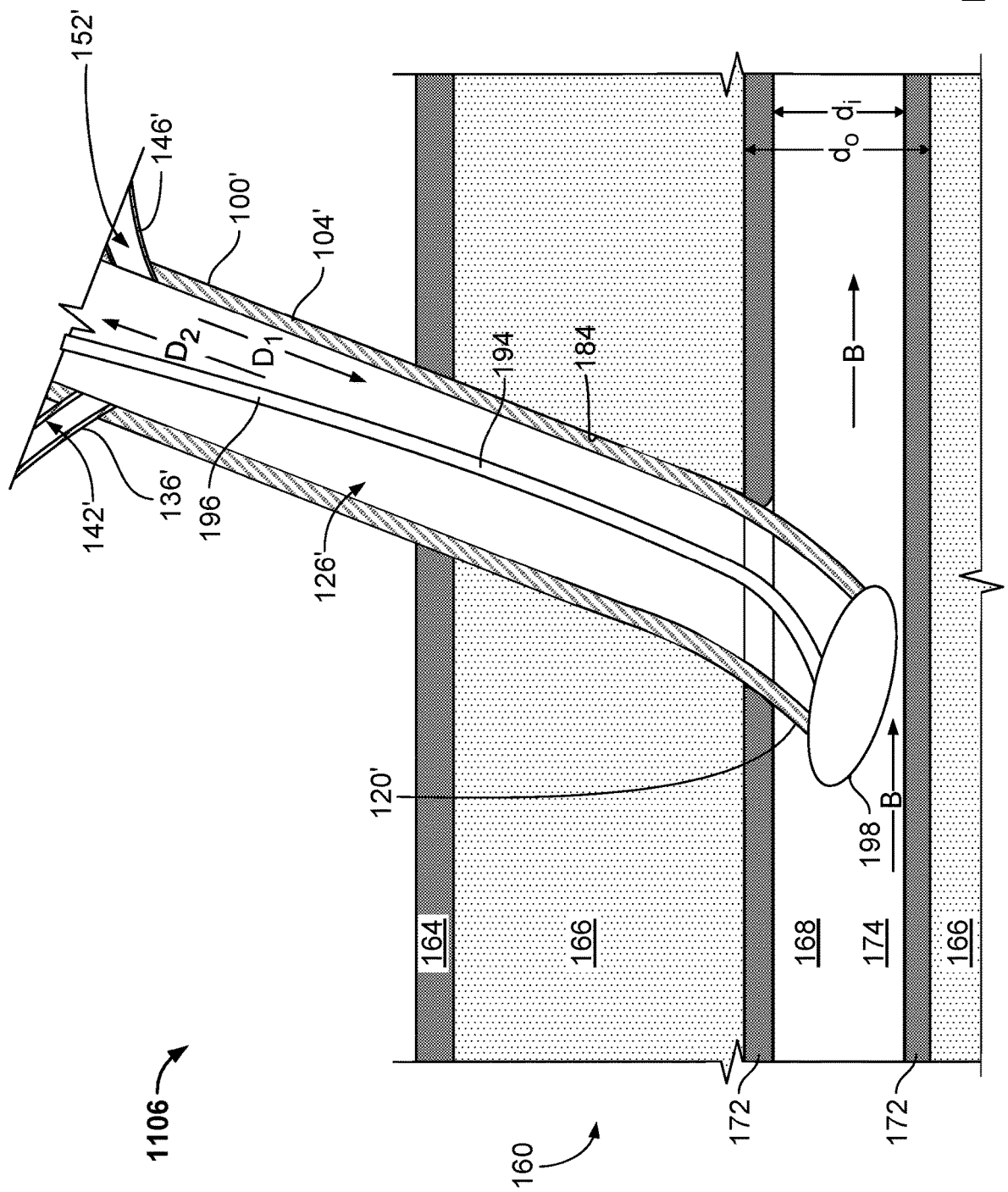
FIG. 13 is a partial cross-sectional view of the alternative vascular access device of FIG. 12 and the positioning catheter of FIGS. 6A-9 and 12 in operation to close the blood vessel of FIGS. 5 and 12 according to the second vascular closure method.
Figure 14:
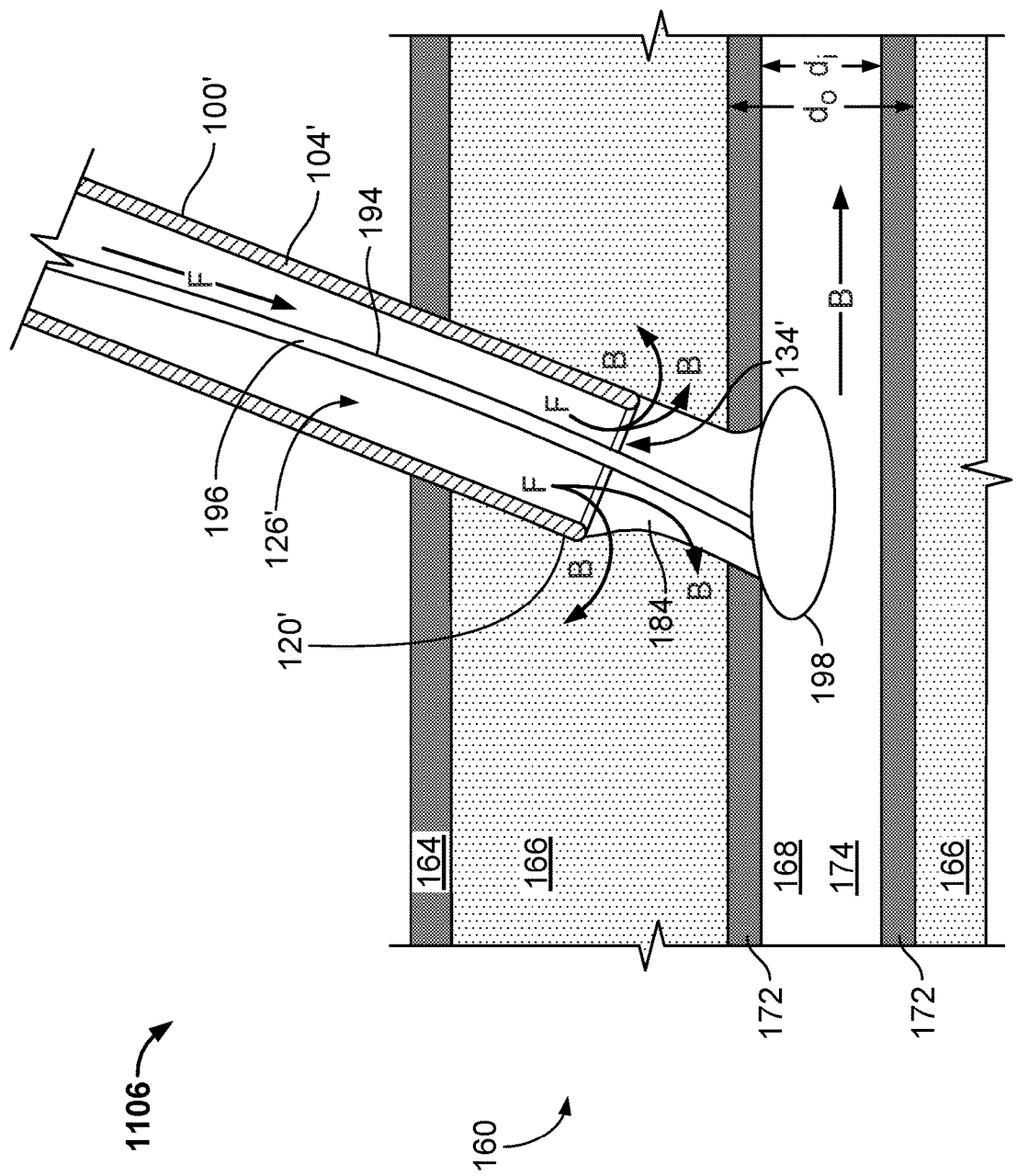
FIG. 14 is a partial cross-sectional view of the alternative vascular access device of FIGS. 12 and 13 and the positioning catheter of FIGS. 6A-9, 12, and 13 in further operation to close the blood vessel of FIGS. 5, 12, and 13 according to the second vascular closure method.

FIGS. 12-18 illustrate various steps of an alternative method 1106 of filling the tissue tract 184 with procoagulant close to the arteriotomy 186, while the sheath 104' has been retracted away from the blood vessel 168 to a proximate position (i.e., spaced apart from the outer diameter $d_o$ of the blood vessel 168). FIG. 12 is substantively identical to FIG. 6A and depicts the introduction of a positioning catheter 194 into the blood vessel 168 via the vascular access device 100', as described in detail above, and FIG. 13 is substantively identical to FIG. 6B and depicts inflation of the balloon 198 and movement of the balloon 198 to a position in which it abuts and seals off the first end 120' of the vascular access device 100'. With reference now to FIG. 14, as an alternative to method 1006 discussed above, in the present method 1106, after the balloon 198 is inflated and positioned to engage the inner diameter $d_i$ of the blood vessel 168 at the arteriotomy 186, the vascular access device 100' is retracted from the blood vessel 168 in second direction Dz. More specifically, with reference to FIG. 14, the vascular access device 100 is moved proximately within the tissue tract 184, such that the first end 120' of the sheath 104' is located away from the blood vessel 168 in the tissue tract 184, between the wall 172 of the blood vessel 168 and the skin 164.

Referring still to FIG. 14, in further operation of method 1106, the tissue tract 184 and the arteriotomy 186 are flushed using the flushing fluid F in the same manner as described above with respect to FIG. 7. By positioning the first end 120' away from the blood vessel 168 in the tissue tract 184, the tissue tract 184 may be well flushed to remove blood of the flow of blood B from the first cavity 126' and the entirety of the tissue tract 184 (without any possibility for blood to remain adhered to surfaces of the sheath 104' near the arteriotomy 186).

Figure 15:
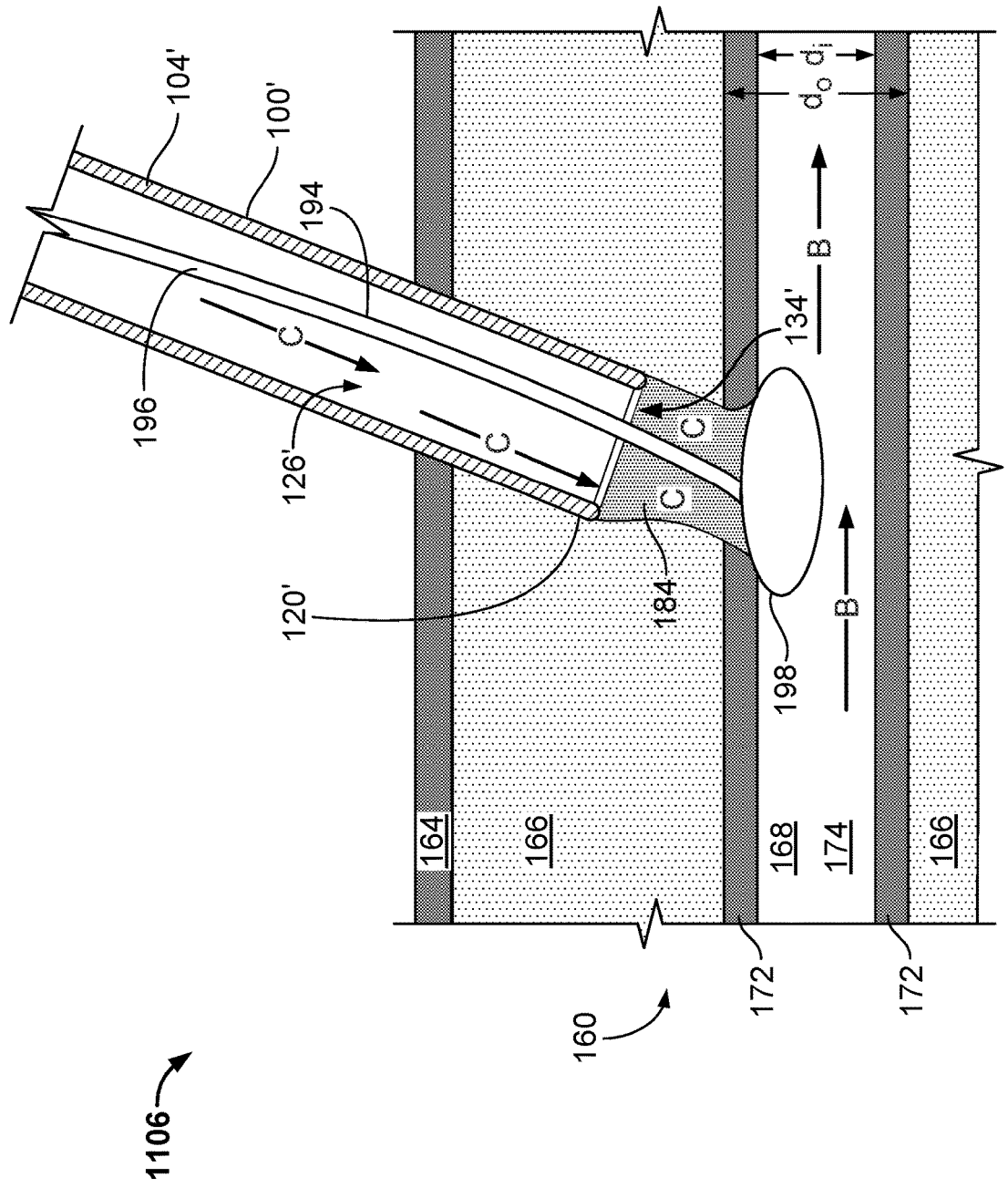
FIG. 15 is a partial cross-sectional view of the alternative vascular access device of FIGS. 12-14 and the positioning catheter of FIGS. 6A-9 and 12-14 in yet further operation to close the blood vessel of FIGS. 5 and 12-14 according to the second vascular closure method.

With reference to FIG. 15, in further operation of method 1106, procoagulant fluid C is introduced after completion of the flushing step via the sheath 104' in the same manner as described above with respect to FIG. 8, so that the procoagulant material C fills the space atop and within the arteriotomy 186 and sits atop the inflated balloon 198.

In various alternative embodiments according to the present disclosure, the procoagulant fluid C could be introduced according to any of the following concepts: at multiple points between the distal and proximal ends of the sheath 104 at the same time; at multiple points between the distal and proximal ends of the sheath 104 at different times; while moving the first end 120 of the sheath 104 from the distal side to the proximal side of the tissue tract 184; and/or while moving the first end 120 of the sheath 104 from the proximal side to the distal side of the tissue tract 184.

Figure 16:
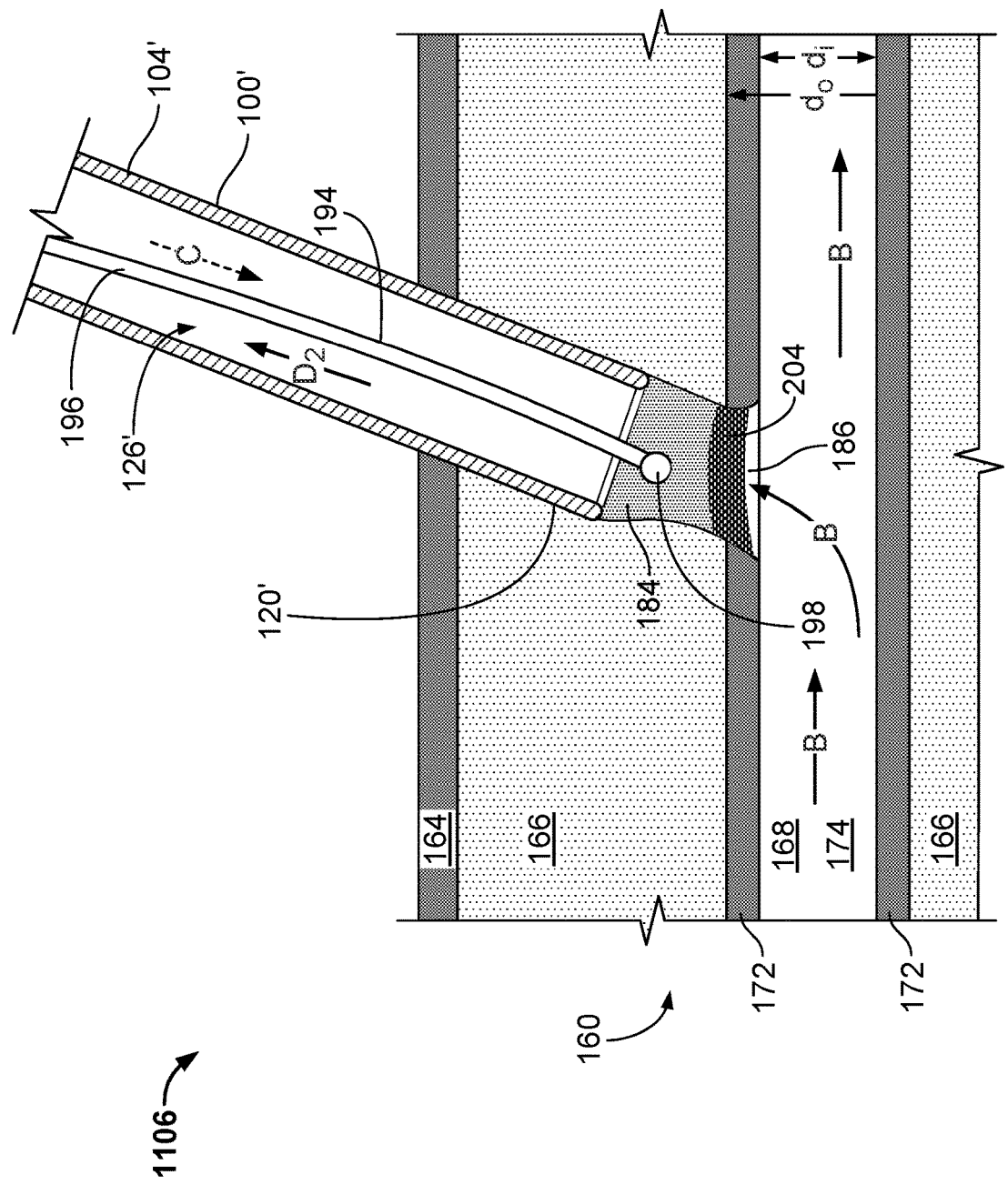
FIG. 16 is a partial cross-sectional view of the alternative vascular access device of FIGS. 12-15 and the positioning catheter of FIGS. 6A-9 and 12-15 in even further operation to close the blood vessel of FIGS. 5 and 12-15 according to the second vascular closure method.

With reference to FIG. 16, in further operation of method 1106, the positioning catheter 194 is now removed from the body part 160 in the same manner as described above with respect to FIG. 9. Specifically, the balloon 198 is deflated and pulled in the second direction $D_2$, through the pooled procoagulant fluid and out of the vascular access device 100'. When the balloon 198 is deflated, a portion of the flow of blood B immediately flows into the arteriotomy 186, where it makes contact with the procoagulant fluid C, thus starting the coagulation process and forming a partially-coagulated plug 204. The remainder of the procoagulant fluid C located in the sheath 104 will also quickly coagulate, starting at the arteriotomy 186 and continuing proximally towards the skin 164.

Figure 17:
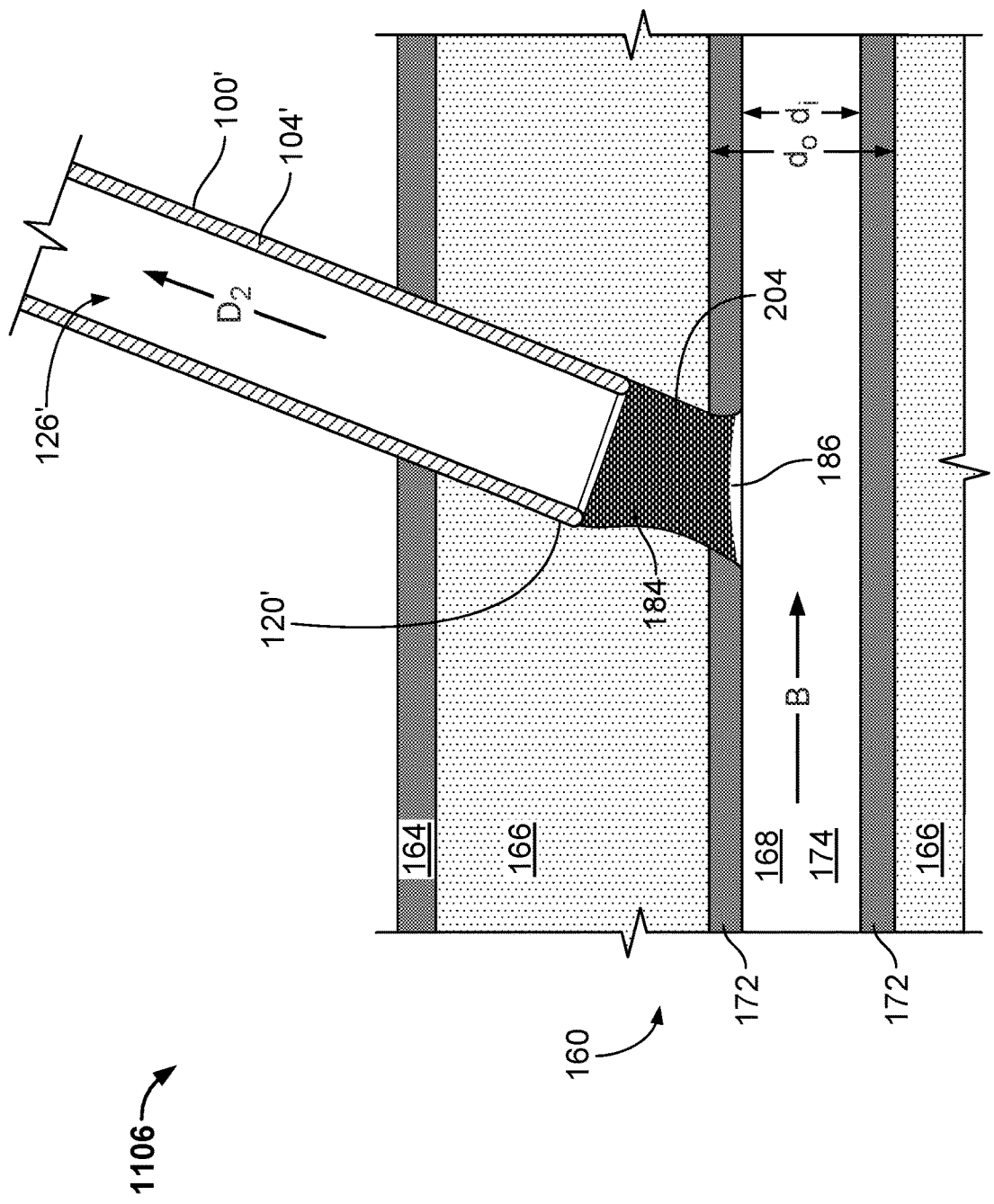
FIG. 17 is a partial cross-sectional view of the exemplary vascular access device of FIGS. 12-16 in yet further operation to close the blood vessel of FIGS. 5 and 12-16 according to the second vascular closure method.

With reference to FIG. 17, in further operation of method 1106, the vascular access device 100 is removed from the body part 160 in the same manner as described above with respect to FIG. 10. If necessary, additional procoagulant material C may optionally be filled within the tissue tract 184 to fill most or all of the tissue tract 184 up to the surface of the skin 164. If additional procoagulant material C is introduced, it may be desirable to ensure that the procoagulant material C is introduced (i.e., in the first direction $D_1$) at a pressure less than the blood pressure in the flow of blood B (i.e., the pressure acting in the second direction $D_2$), to minimize the risk of the procoagulant material C entering the blood vessel 168 and possibly causing an embolic event.

Figure 18:
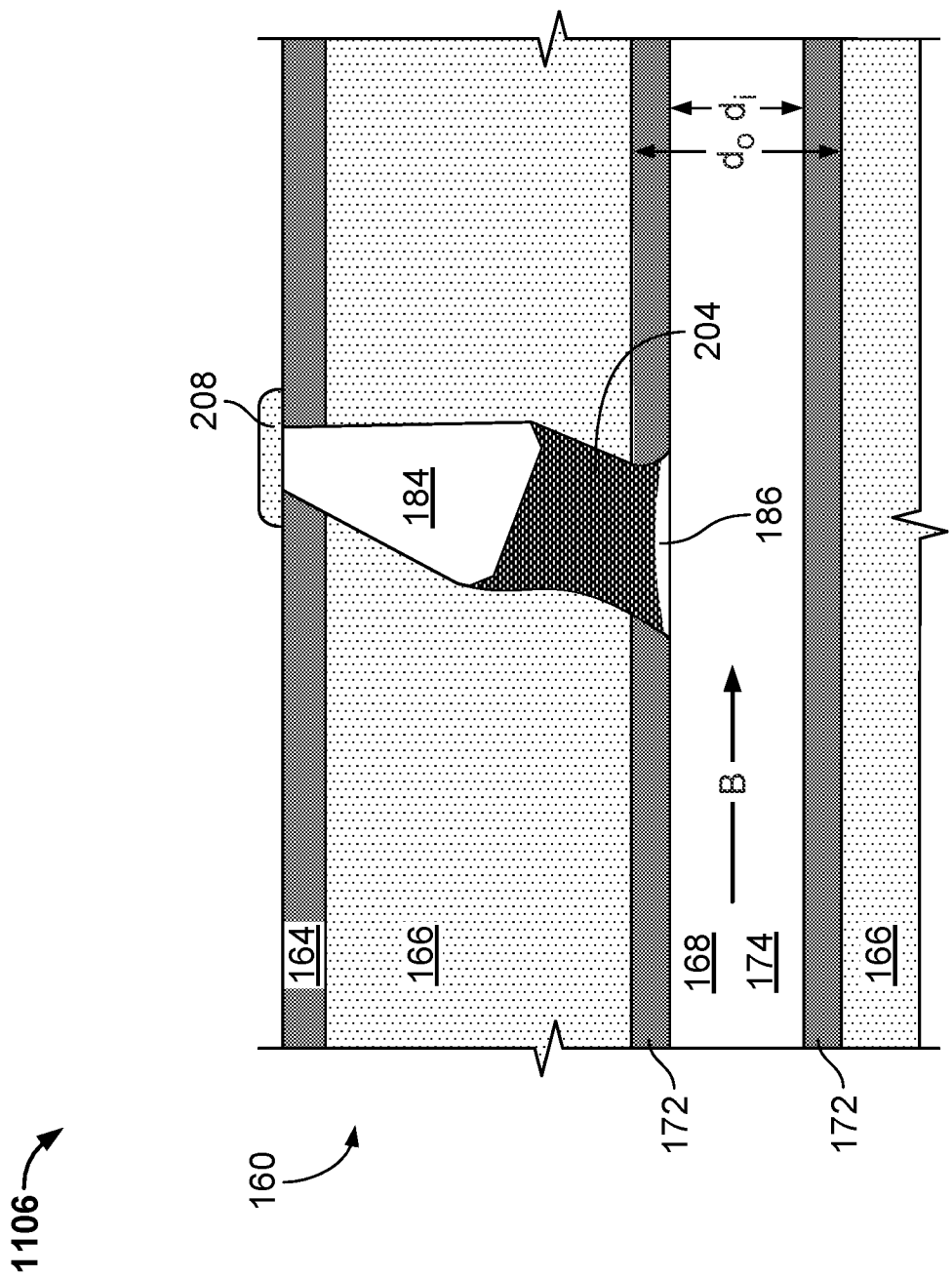
FIG. 18 is a partial cross-sectional view of the bandage of FIG. 11 in operation to close the body part of FIGS. 4-17 according to the second vascular closure method.
Figure 19:
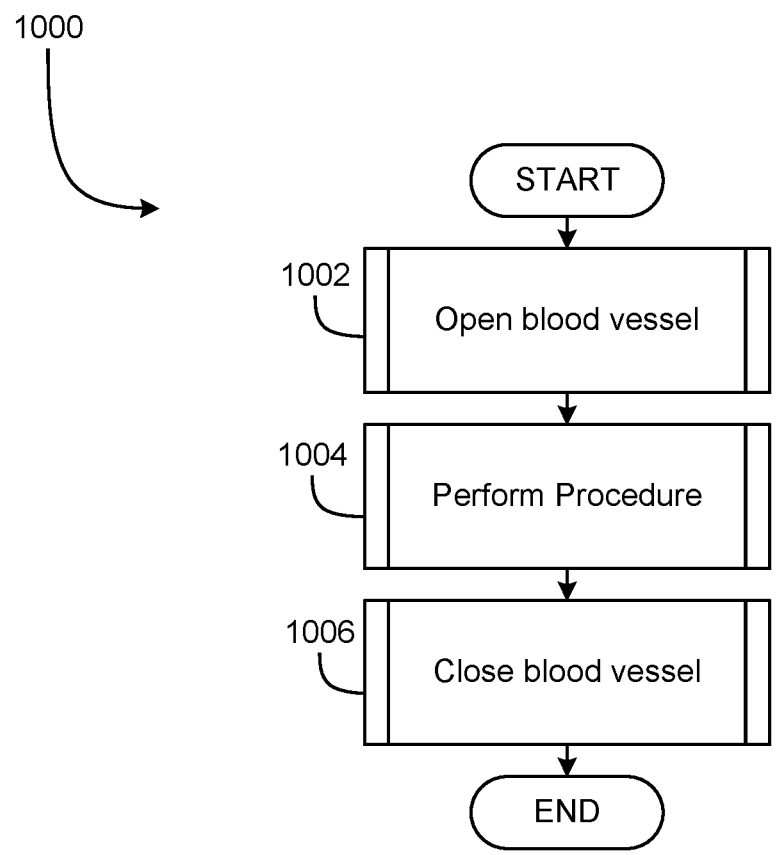
FIG. 19 is a flowchart representative of a first method according to the present disclosure of performing an internal vascular procedure utilizing a known vascular access method and the first vascular closure method of FIGS. 6A-11.

Finally, with reference to FIG. 18, the bandage 208 may be applied to the skin 164 to cover and close the tissue tract 184 in the same manner as described above with respect to FIG. 11. FIG. 19 is a flowchart of a first exemplary method 1000 to perform a vascular access and closure procedure utilizing a known vascular access method (e.g., the ST) and the vascular closure method illustrated in FIGS. 6A-11. Further, although the exemplary method 1000 is described with reference to the flowchart illustrated in FIG. 19, additional or alternative method steps to perform the vascular access and closure procedures are possible. For example, the order of execution of the blocks may be changed, and/or some of the blocks described may be changed, eliminated, or combined.

With reference to FIG. 19, the first exemplary method 1000 includes collected process blocks 1002, 1004, and 1006. Each of the collected process blocks 1002, 1004, and 1006 includes multiple blocks representing individual steps, as will be described in greater detail below. Generally, the first exemplary method 1000 begins at collected process block 1002 by opening or accessing the blood vessel 168, for example via use of the ST. Next, the first exemplary method 1000 generally continues at collected process block 1004 by performing a procedure within the blood vessel 168. Then, the first exemplary method 1000 generally continues at collected process block 1006 by closing the blood vessel 168 according to the vascular closure method 1006 described herein.

Figure 20:
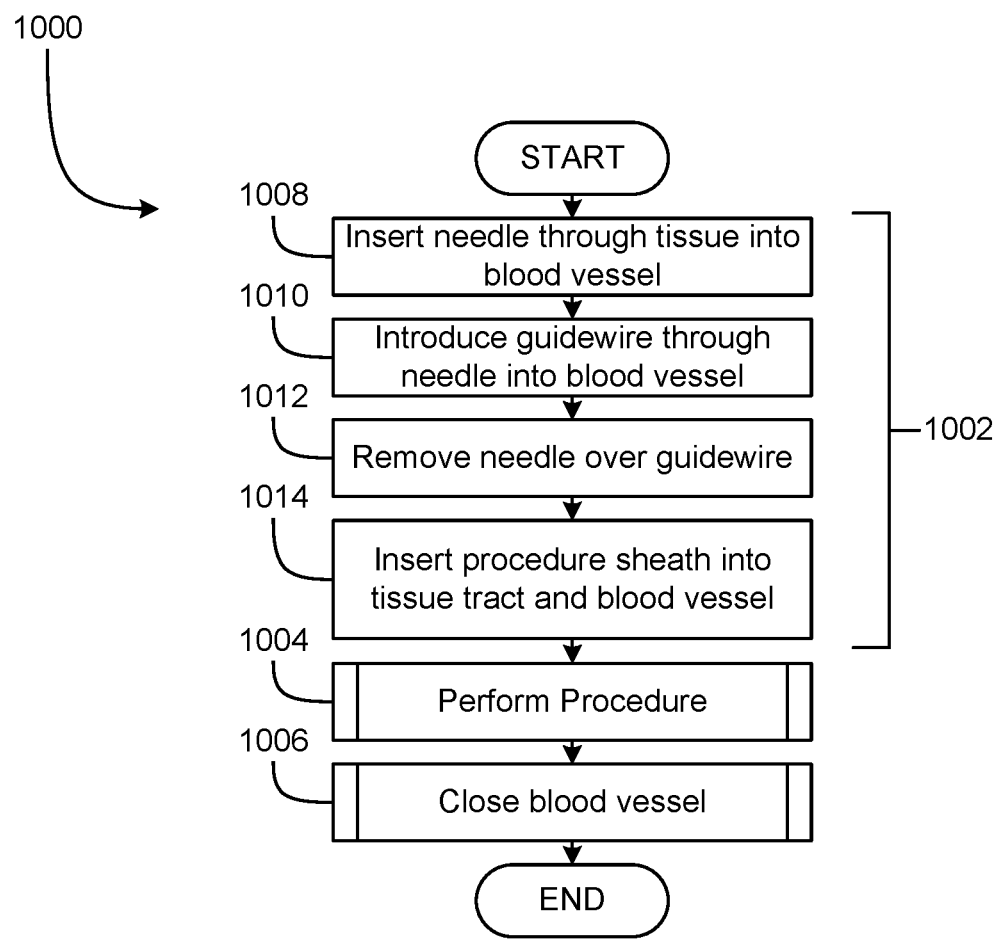
FIG. 20 illustrates the flowchart of FIG. 19 with a first block of the flowchart expanded.

With reference to FIG. 20, the collected process block 1002 includes blocks 1008-1014. At block 1008, a needle is inserted through tissue 166 into the blood vessel 168 as described above, e.g., in accordance with the ST. At block 1010, a guidewire is introduced through the interior of the needle and placed interior to the blood vessel 168, as described above, e.g., in accordance with the ST. At block 1012, the needle is removed over the guidewire, leaving the guidewire in place within the tissue tract 184 and blood vessel 168 to maintain vascular access. Finally, at block 1014, a procedure sheath is introduced into the tissue tract 184 and blood vessel 168.

Figure 21:
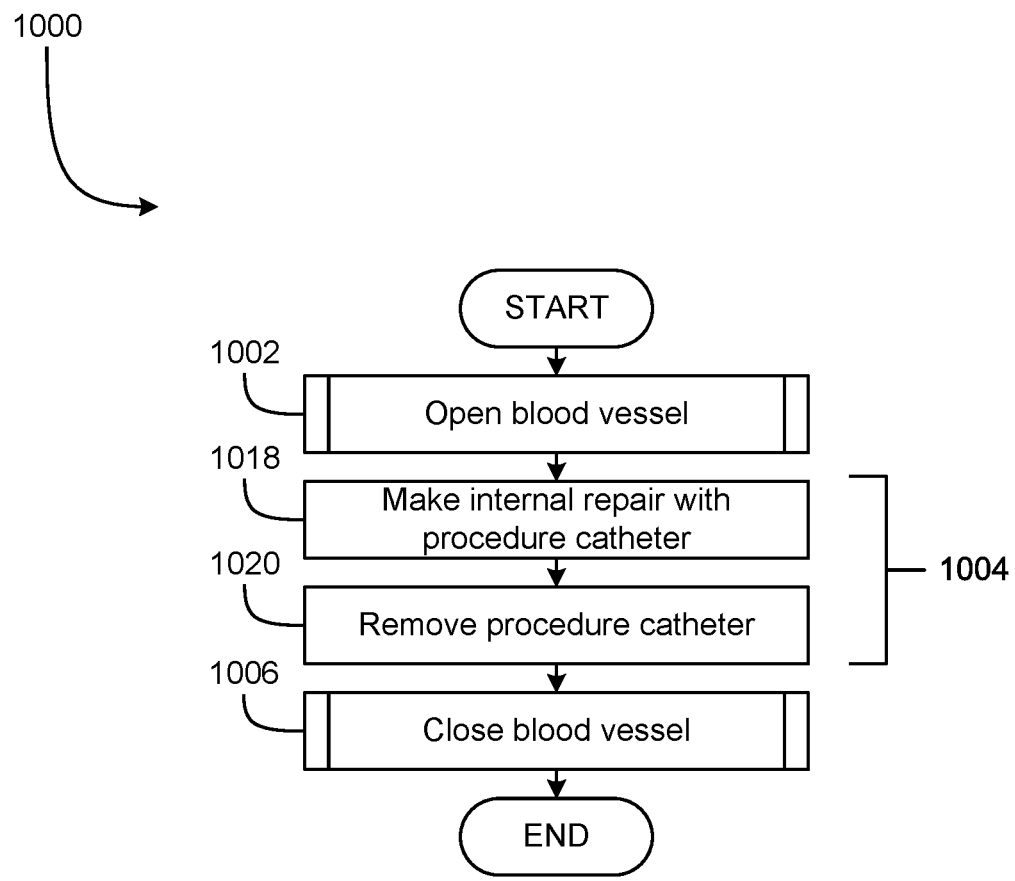
FIG. 21 illustrates the flowchart of FIG. 19 with a second block of the flowchart expanded.

With reference to FIG. 21, the collected process block 1004 includes blocks 1018 and 1020. At block 1018, the procedure catheter 190 and/or other tool(s) are used to make an internal repair as described above. At block 1020, the procedure catheter 190 is removed from the blood vessel 168 and the tissue tract 184 as described above.

Figure 22:
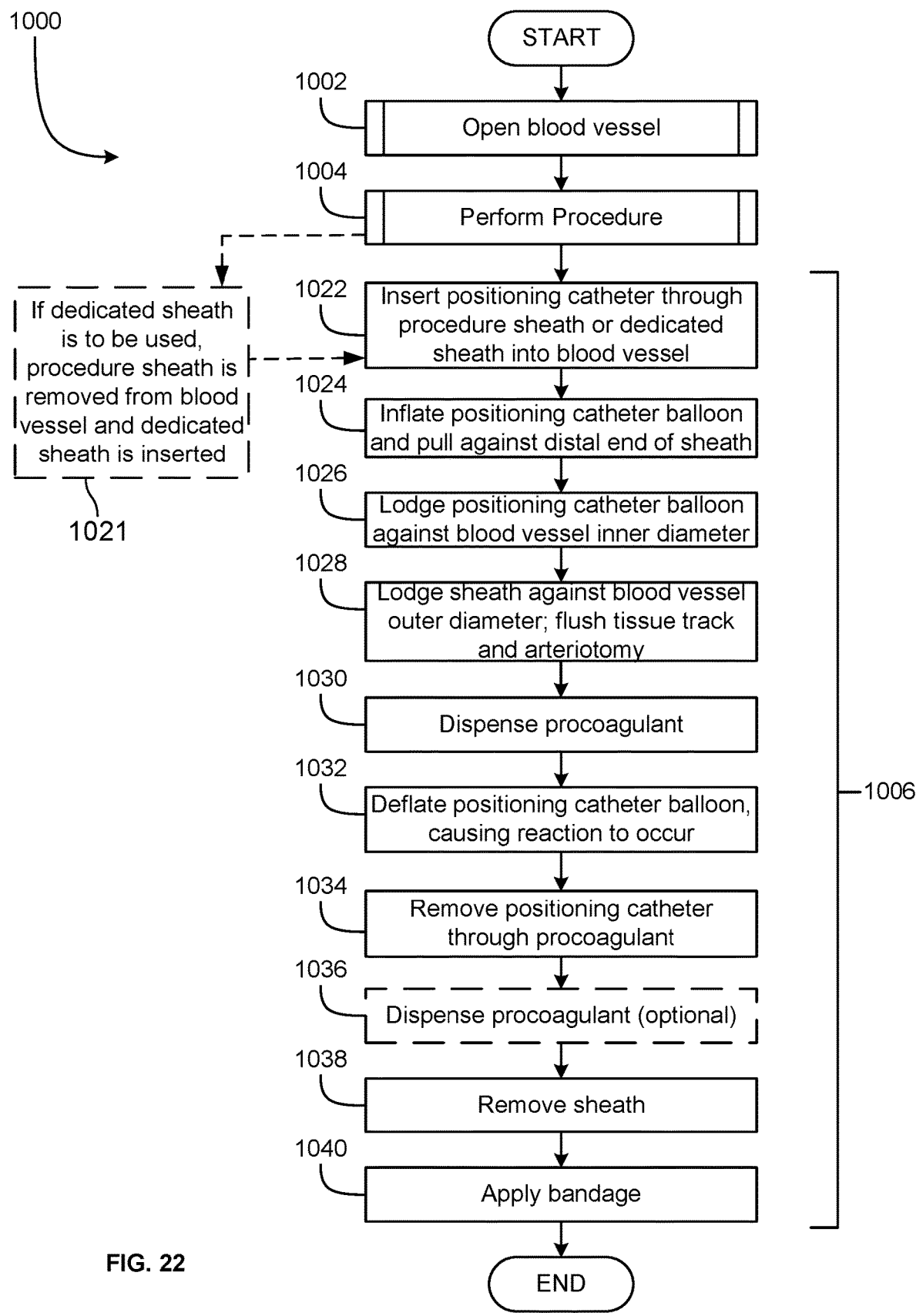
FIG. 22 illustrates the flowchart of FIG. 19 with a third block of the flowchart expanded.

With reference to FIG. 22, the collected process block 1006 includes blocks 1022-1040. If a dedicated sheath, e.g., sheath 104, is to be used to perform the closure method 1006 according to the present disclosure, the procedure sheath, e.g., sheath 104', is removed from the blood vessel 168 and the dedicated sheath is inserted into the blood vessel 168—shown via block 1021 in FIG. 22—prior to insertion of the positioning catheter. At block 1022, the positioning catheter 194 is inserted through the sheath 104 or sheath 104' into the blood vessel 168 as described above with reference to FIG. 6A.

At block 1024, the balloon 198 of the positioning catheter 194 is inflated as described above with reference to FIG. 6B and pulled against the distal end of the sheath 104,104' while located interior to the blood vessel 168. At block 1026, the balloon 198 of the positioning catheter 194 is lodged against the inner diameter $d_i$ of the blood vessel 168 as described above with reference to FIG. 7. At block 1028, the sheath 104, 104' is lodged against or placed very near the outer diameter outer diameter $d_o$ of the blood vessel 168, and the tissue tract 184 and arteriotomy 186 are flushed using the flushing fluid F as described above with reference to FIG. 7. At block 1030, the procoagulant fluid C is dispensed as described above with reference to FIG. 8.

At block 1032, the positioning catheter balloon 198 is deflated as described above with reference to FIG. 9, which immediately causes blood B from the blood vessel 168 to flow through the arteriotomy 186 and react with the procoagulant fluid C. At block 1034, the positioning catheter 194 is removed through the procoagulant fluid C and removed from the sheath 104,104' as described above with reference to FIG. 9. At block 1036, if blood oozing is confirmed, the procoagulant fluid C is optionally dispensed again as described above with reference to FIG. 10. At block 1038, the sheath 104,104' is removed from the body part 160 as described above with reference to FIG. 10. Finally, at block 1040, the bandage 208 is applied to the skin 164 as described above with reference to FIG. 11, to complete the vascular closure method 1006.

Figure 23:
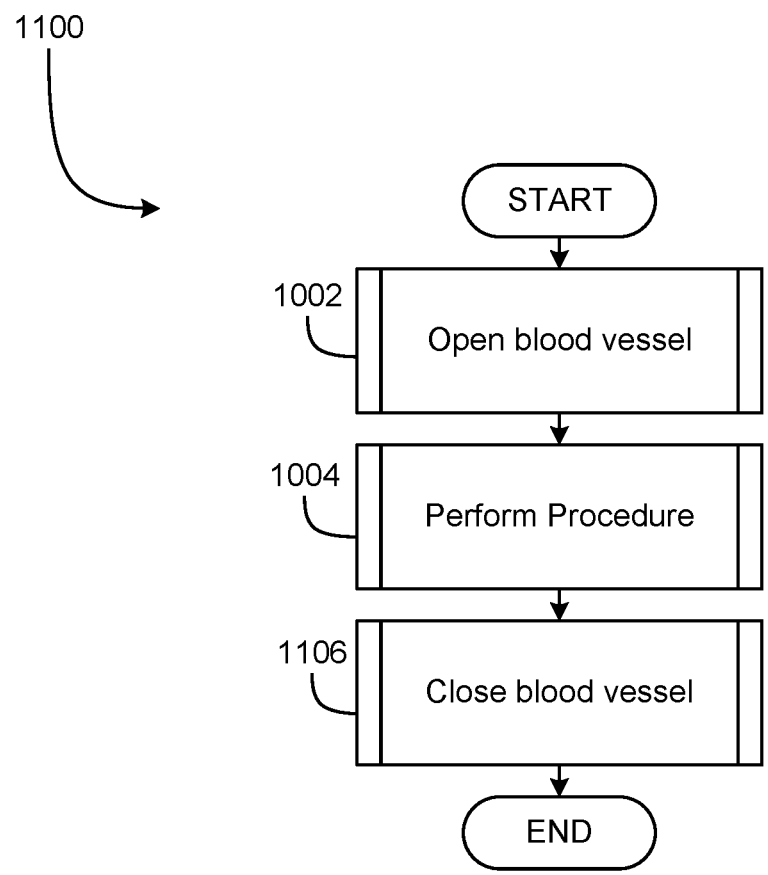
FIG. 23 is a flowchart representative of a second method according to the present disclosure of performing an internal vascular procedure utilizing a known vascular access method and the second vascular closure method of FIGS. 12-18.

FIG. 23 is a flowchart of a second exemplary method 1100 to perform a vascular access and closure procedure utilizing a known vascular access method (e.g., the ST) and the vascular closure method illustrated in FIGS. 12-18. Further, although the second exemplary method 1100 is described with reference to the flowchart illustrated in FIG. 23, additional or alternative method steps to perform the vascular access and closure procedures are possible. For example, the order of execution of the blocks may be changed, and/or some of the blocks described may be changed, eliminated, or combined.

With reference to FIG. 23, the second exemplary method 1100 includes the collected process blocks 1002 and 1004 as described above with reference to FIGS. 19-21, and further includes collected process block 1106. The collected process block 1106 includes multiple blocks representing individual steps, as will be described in greater detail below. Generally, the second exemplary method 1100 begins at collected process block 1002 by opening or accessing the blood vessel 168, for example via use of the ST. Next, the second exemplary method 1100 generally continues at collected process block 1004 by performing a procedure within the blood vessel 168. Then, the second exemplary method 1100 generally continues at collected process block 1106 by closing the blood vessel 168 according to the vascular closure method 1106 described herein.

Figure 24:
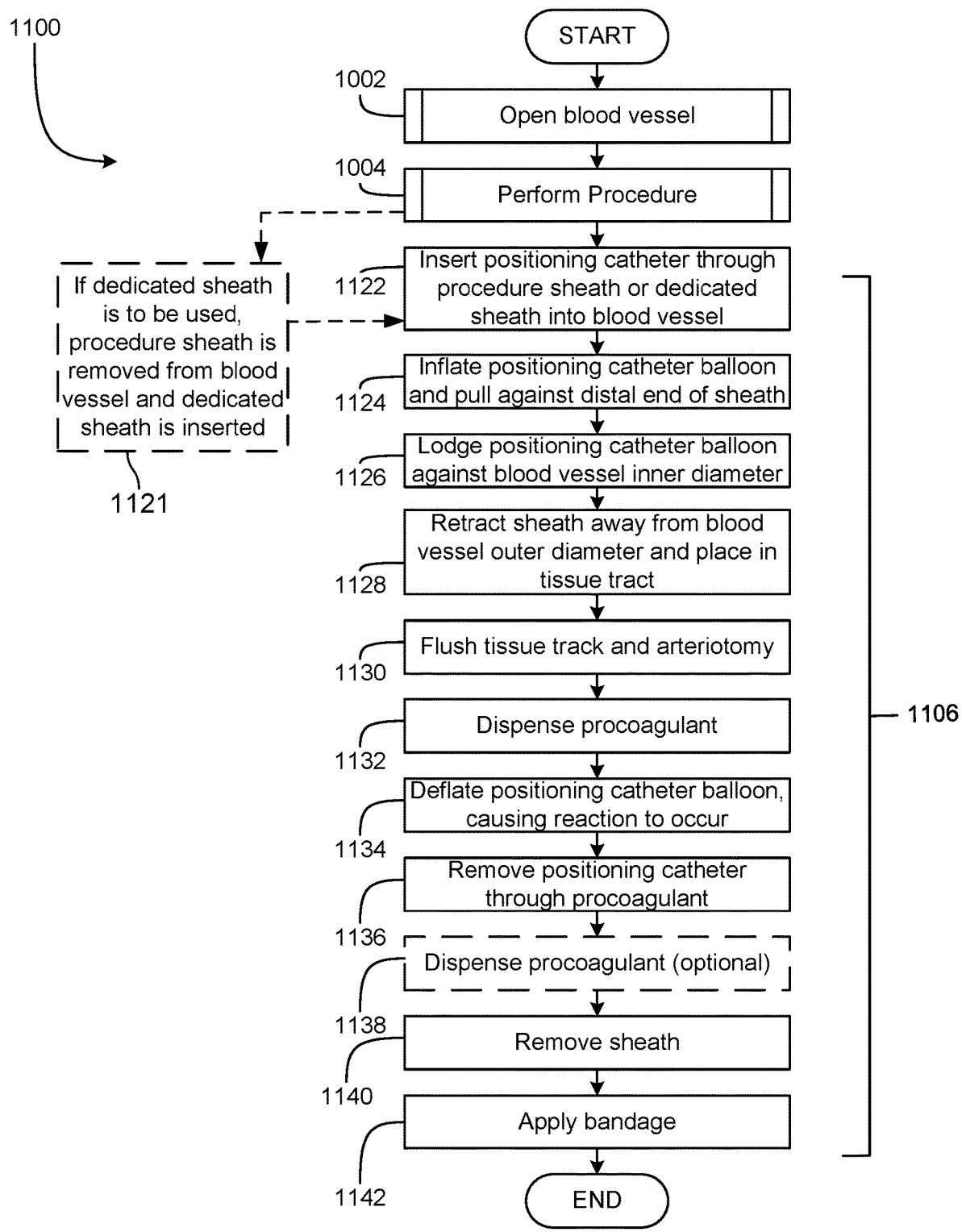
FIG. 24 illustrates the flowchart of FIG. 23 with a block of the flowchart expanded.

With reference to FIG. 24, the collected process block 1106 includes blocks 1122-1142. If a dedicated sheath, e.g., sheath 104, is to be used to perform the closure method 1106 according to the present disclosure, the procedure sheath, e.g., sheath 104', is removed from the blood vessel 168 and the dedicated sheath is inserted into the blood vessel 168— shown via block 1121 in FIG. 24—prior to insertion of the positioning catheter. At block 1122, the positioning catheter 194 is inserted through the sheath 104 or sheath 104' into the blood vessel 168 as shown in FIG. 12 and described above with reference to FIG. 6A.

At block 1124, the balloon 198 of the positioning catheter 194 is inflated as described above with reference to FIG. 13 and pulled against the distal end of the sheath 104,104' while located interior to the blood vessel 168. At block 1126, the positioning catheter balloon 198 is lodged against the inner diameter $d_i$ of the blood vessel 168 as described above with reference to FIG. 13.

At block 1128, the sheath 104,104' is retracted from the blood vessel 168 to position the first end 120,120' of the sheath 104,104' spaced apart from the blood vessel wall 172 in the tissue tract 184, as described above with reference to FIGS. 13 and 14. At block 1130, the tissue tract 184 and arteriotomy 186 are flushed using the flushing fluid F as described above with reference to FIG. 14. At block 1132, the procoagulant fluid C is dispensed as described above with reference to FIG. 15.

At block 1134, the balloon 198 of the positioning catheter 194 is deflated as described above with reference to FIG. 16, which immediately causes blood B from the blood vessel 168 to flow through the arteriotomy 186 and react with the procoagulant fluid C. At block 1136, the positioning catheter 194 is removed through the procoagulant fluid C and removed from the sheath 104,104' as described above with reference to FIG. 16. At block 1138, if blood oozing is confirmed, the procoagulant fluid C is optionally dispensed again as described above with reference to FIG. 16. At block 1140, the sheath 104,104' is removed from the body part 160 as described above with reference to FIG. 17. Finally, at block 1142, the bandage 208 is applied to the skin 164 as described above with reference to FIG. 18, to complete the vascular closure method 1106.

Within this specification, embodiments have been described in a way which enables a clear and concise specification to be written, but it is intended and will be appreciated that embodiments may be variously combined or separated without departing from the inventive concept. For example, it will be appreciated that all preferred features described herein are applicable to all aspects of the inventive concept described herein.

Thus, while the inventive concept has been described in connection with particular embodiments and examples, the inventive concept is not necessarily so limited, and that numerous other embodiments, examples, uses, modifications, and departures from the embodiments, examples, and uses are intended to be encompassed by the claims attached hereto. Further, the entire disclosure of each patent and publication cited herein is incorporated by reference as if each such patent or publication were individually incorporated by reference herein.

While the principles of the claimed invention have been described above in connection with specific embodiment(s), it is to be clearly understood that this description is made only by way of example and not as a limitation of the scope of the invention, as set forth in the appended claims.

What is claimed is:

1. A method of performing a vascular closure procedure at a vascular access site that has been formed through a wall of a blood vessel in a body part of a patient, the method comprising:
   inserting a sheath into a tissue tract defined in the body part to abut an end of the sheath against the wall of the blood vessel, the tissue tract being in fluid flow communication with an interior of the blood vessel via the vascular access site such that blood from the blood vessel may enter the tissue tract;
   temporarily sealing the vascular access site so that blood from the blood vessel may no longer enter the tissue tract;
   flushing the tissue tract with a flushing fluid via the sheath such that the tissue tract is substantially cleared of blood;
   retracting the sheath to position the end of the sheath in the tissue tract spaced apart from the wall of the blood vessel;

after the retracting step occurs, injecting a procoagulant material into the tissue tract via the sheath at a location adjacent the vascular access site; and unsealing the vascular access site so that blood from the blood vessel interacts with the procoagulant material at the location.

2. The method of claim 1, wherein the step of inserting the sheath into the tissue tract further comprises inserting the sheath into the tissue tract to abut an end of the sheath against the wall of the blood vessel, and wherein the steps of flushing the tissue tract and injecting a procoagulant material occur while the sheath is in this position.

3. The method of claim 1, further comprising inserting a positioning catheter into the blood vessel via the sheath, the positioning catheter comprising a balloon or anchor, the balloon and anchor each having a first configuration capable of performing the step of temporarily sealing the vascular access site and a second configuration capable of performing the step of unsealing the vascular access site.

4. The method of claim 3, wherein the step of temporarily sealing the vascular access site further comprises inflating a balloon of the positioning catheter inside the interior of the blood vessel and placing the positioning catheter under tension so that the inflated balloon presses against an interior surface of the wall of the blood vessel while covering the vascular access site.

5. The method of claim 4, further comprising deflating the balloon of the positioning catheter while inside the interior of the blood vessel.

6. The method of claim 5, wherein the at least a portion of the procoagulant material that is delivered to the location adjacent the vascular access site acts to coagulate blood located in the tissue tract into a plug, the method further comprising pulling the deflated balloon through the plug.

7. The method of claim 6, further comprising injecting additional procoagulant material into the tissue tract via the sheath after the step of pulling the balloon through the plug.

8. The method of claim 5, further comprising removing the balloon from the sheath immediately after the step of deflating the balloon.

9. The method of claim 1, wherein the step of inserting the sheath into the tissue tract further includes placing one or more openings that are located adjacent an end of the sheath adjacent to the vascular access site prior to the step of flushing the tissue tract, wherein the step of flushing the tissue tract further comprises running the flushing fluid through the sheath and out of the one or more openings to substantially clear the tissue tract of blood.

10. The method of claim 1, wherein the step of injecting a procoagulant material occurs from a plurality of different locations located on the sheath.

11. The method of claim 10, wherein the step of injecting a procoagulant material occurs from the plurality of different locations simultaneously.

12. The method of claim 10, wherein the step of injecting a procoagulant material occurs from the plurality of different locations at different times.

13. The method of claim 1, wherein the step of injecting a procoagulant material further comprises injecting the procoagulant material into the tissue tract via a secondary nozzle that has been introduced through the sheath.

14. The method of claim 13, further comprising locating a distal end of the secondary nozzle beyond a distal end of the sheath prior to or during the step of injecting a procoagulant material.

15. The method of claim 13, wherein the step of injecting a procoagulant material further comprises moving the secondary nozzle away from the vascular access site while the step of injecting a procoagulant material is occurring.

16. The method of claim 13, wherein the step of injecting a procoagulant material further comprises moving the secondary nozzle towards the vascular access site while the step of injecting a procoagulant material is occurring.

17. The method of claim 1, further comprising, after the step of injecting a procoagulant material, monitoring for blood leakage and performing a second injecting step in which a procoagulant material is introduced into the tissue tract if blood leakage is detected.

18. The method of claim 1, wherein the step of injecting a procoagulant material comprises injecting a procoagulant material and a solvent material at the location.

19. The method of claim 18, wherein the step of injecting a procoagulant material comprises injecting the procoagulant material and the solvent material at the location simultaneously.

20. The method of claim 18, wherein the step of injecting a procoagulant material comprises injecting the procoagulant material and the solvent material at the location at different times.

21. The method of claim 18, wherein the step of injecting a procoagulant material comprises injecting the procoagulant material and the solvent material at the location at alternating times.

22. The method of claim 1, wherein the step of injecting a procoagulant material comprises injecting a procoagulant material and a solvent material at the location, wherein the procoagulant material is comprised of cyanoacrylate and the solvent material is comprised of dimethyl sulfoxide.

23. A method of performing a vascular closure procedure at a vascular access site that has been formed through a wall of a blood vessel in a body part of a patient, the method comprising:

inserting a sheath into a tissue tract defined in the body part, the tissue tract being in fluid flow communication with an interior of the blood vessel via the vascular access site such that blood from the blood vessel may enter the tissue tract;

inserting a positioning catheter through the sheath into the blood vessel, the positioning catheter comprising a cavity and a nozzle slidably attached thereto such that a position of a distal end of the nozzle is adjustable with respect to a distal end of the cavity;

temporarily sealing the vascular access site so that blood from the blood vessel may no longer enter the tissue tract;

flushing the tissue tract with a flushing fluid via the sheath or the nozzle such that the tissue tract is substantially cleared of blood;

locating the distal end of the nozzle spaced apart from the wall of the blood vessel;

after the locating step occurs, injecting a procoagulant material into the tissue tract via the nozzle at a location adjacent the vascular access site; and unsealing the vascular access site so that blood from the blood vessel interacts with the procoagulant material at the location.

* * * * *

UNITED STATES PATENT AND TRADEMARK OFFICE
CERTIFICATE OF CORRECTION

PATENT NO. : 11,766,544 B2
APPLICATION NO. : 16/864865
DATED : September 26, 2023
INVENTOR(S) : Junya Kojima It is certified that error appears in the above-identified patent and that said Letters Patent is hereby corrected as shown below:

In the Specification

Column 11 Line 14, "$D_z$" should be --$D_2$--.

Signed and Sealed this
Twelfth Day of December, 2023

Katherine Kelly Vidal
*Director of the United States Patent and Trademark Office*